US010078050B2

(12) United States Patent
Kapit et al.

(10) Patent No.: US 10,078,050 B2
(45) Date of Patent: Sep. 18, 2018

(54) SUBMERSIBLE N-WAVELENGTH INTERROGATION SYSTEM AND METHOD FOR MULTIPLE WAVELENGTH INTERFEROMETERS

(71) Applicant: Woods Hole Oceanographic Institution, Woods Hole, MA (US)

(72) Inventors: Jason A. Kapit, Pocasset, MA (US); Raymond W. Schmitt, Falmouth, MA (US); Norman E. Farr, Woods Hole, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 0 days.

(21) Appl. No.: 15/227,253

(22) Filed: Aug. 3, 2016

(65) Prior Publication Data
US 2017/0030830 A1 Feb. 2, 2017

Related U.S. Application Data

(63) Continuation-in-part of application No. 14/166,650, filed on Jan. 28, 2014, now Pat. No. 9,441,947.
(Continued)

(51) Int. Cl.
*G01J 3/00* (2006.01)
*G01N 21/45* (2006.01)
(Continued)

(52) U.S. Cl.
CPC ........... *G01N 21/45* (2013.01); *G01B 9/0209* (2013.01); *G01B 9/02041* (2013.01);
(Continued)

(58) Field of Classification Search
CPC ................ G01J 9/02; G01J 3/26; G01J 3/00
See application file for complete search history.

(56) References Cited

U.S. PATENT DOCUMENTS 7,564,562 B2 7/2009 Choi
9,441,947 B2 * 9/2016 Kapit ................ G01B 9/02041
(Continued)

OTHER PUBLICATIONS

Alford, M. H., D. W. Gerdt, C. M. Adkins. (2006) "An Ocean Refractometer: Resolving Millimeter-Scale Turbulent Density Fluctuations via the Refractive Index," J. Atmos. Oceanic Technol., 23, 121-137.
(Continued)

*Primary Examiner* — Jonathan Hansen
(74) *Attorney, Agent, or Firm* — Goodwin Procter LLP

(57) ABSTRACT

In an in situ interrogation system for multiple wavelength interferometers a fringe spectrum that includes non-quadrature-spaced radiation-intensity samples is analyzed to obtain a high resolution relative phase measurement of the optical path length difference associated with the fringe spectrum. The fringe spectrum can be analyzed to obtain a fringe number and a quadrant as well, which can be combined with the relative phase measurement to obtain a high precision measurement of the absolute optical path length difference. An environmental condition corresponding to the absolute optical path length difference can be measured using the measurement of the absolute optical path length difference including salinity, pressure, density, and refractive index of a medium.

16 Claims, 16 Drawing Sheets

Related U.S. Application Data

(60) Provisional application No. 61/757,465, filed on Jan. 28, 2013.

(51) Int. Cl.
    *G01N 21/25*     (2006.01)
    *G01B 9/02*     (2006.01)
    *G01D 5/26*     (2006.01)

(52) U.S. Cl.
    CPC ......... *G01B 9/02044* (2013.01); *G01D 5/266* (2013.01); *G01N 21/25* (2013.01)

(56) References Cited

U.S. PATENT DOCUMENTS

| | | | |
|---|---|---|---|
| 2003/0094281 A1* | 5/2003 | Tubel | E21B 47/00 166/250.03 |
| 2005/0151975 A1* | 7/2005 | Melnyk | G01B 11/18 356/480 |
| 2009/0219542 A1 | 9/2009 | Waegli et al. | |

OTHER PUBLICATIONS

Breen, S., et al. (1990) "Fiber optic displacement sensor with subangstrom resolution," Dalhousie University, Applied Optics, vol. 29, No. 1, pp. 1-18.

Calatroni J., et al. (1996) "Spectrally-resolved white-light interferometry as a profilometry tool," Optics and Laser Technolgy, vol. 28, No. 7, pp. 485-489.

Calatroni, J., et al. (1996) "Spectrally-resolved white-light interferometry as a profilometry tool," Optics & Laser Technolgy, vol. 28, No. 7, pp. 485-489.

Chang, C., et al. (1996) "Multiplexed Optical Fiber Sensors Using a Single Fabry-Perot Resonator for Phase Modulation," Journal of Lightwave Technology, vol. 14, No. 7, pp. 1653-1663.

Cortes, R., et al. (1998) "Interferometric fiber-optic temperature sensor with spiral polarizatoin couplers," Optics Communications, vol. 154, pp. 268-272.

Debnath, S. K., et al. (2006) "Improved Optical Profiling Using the Spectral Phase in Spectrally Resolved White-Light Interferometry," Applied Optics, vol. 45, No. 27, pp. 6965-6972.

Duan, D., et al. (2011) "In-Fiber Fabry-Perot and Mach-SZehnder interferometers based on hollow optical fiber fabricated by arc fusion splicing with small lateral offsets," Optics Communications, vol. 284, pp. 5311-5314.

Egorov, S., et al. (1995) "Spectral Signal Processing in Intrinsic Interferometric Sensors Based on Birefringent Polaraization-Maintaining Optical Fibers," Journal of Lightwaver Technology, Vo. 13, No. 7, pp. 1231-1236.

Ezbiri, A., et al. (1997) Five wavelength interrogation technique for miniature fibre optic Fabry-Perot sensors, Optic Communications, vol. 133, pp. 62-66.

Gangopadhyay, T. K. (2004) "Non-contact vibration measurement based on an extrinsic Fabry-Perot interferometer implemented using arrays of single-mode fibres," Measurement Science and Technology, vol. 15, pp. 911-917.

Grosso, P. M. Le Menn, J.-L. de Bougrenet de la Tocnaye, Z. Y. Wu, D. Malardé, (2010) "Practical versus absolute salinity measurements: New advances in high performance seawater salinity sensors," Deep-Sea Research, 57, 151-156.

Hart, M., et al. (1998) "Fast Surface Profiling by Spectral Analysis of White-Light Interferograms With Fourier Transform Spectroscopy," Applied Optics, vol. 37, No. 10, pp. 1764-1769.

Hart, M., et al. (1998) "Fast surface profiling by spectral analysis of white-light interferograms with Fourier transform spectroscopy," vol. 37, No. 10, pp. 1764-1769.

Hoang, T., et al. (2011) "Phase extraction from optical interferograms in presence of intensity nonlinearity and arbitrary phase shifts," Applied Physics Letters, vol. 99, (4 pages).

International Search Report and Written Opinion for International Patent Application No. PCT/US2014/013430 dated May 30, 2014, 11 pages.

Jackson, D., et al. (1982) "Pseudoheterodyne Detection Scheme for Optical Interferometers," Electronic Letters, vol. 18, No. 25, pp. 1081-1083.

Liu, T., et al. (2000) "A frequency division multiplexed low-finesse fiber optic Fabry-Perot sensor system for strain and displacement measurements," Review of Scientific Instruments, vol. 71, No. 3, pp. 1275-1278.

Lo, Y., et al. (2001) "Differential optical fiber refractometer based on a path-matching differential interferometer with temperature compensation," Applied Optics, vol. 40, No. 21, pp. 3518-3524.

McDougall, T. J. and P. M. Barker. (2011) "Getting started with TEOS-10 and the Gibbs Seawater (GSW)" Oceanographic Toolbox.

Millard, R. C. and G. Seaver. (1990) "An index of refraction algorithm for seawater over temperature, pressure, salinity, density, and wavelength," Deep-Sea Research 37, 1909-1926.

Murphey, K., et al. (1991) "Quadrature phase-shifted, extrinsic Fabry-Perot optical fiber sensors," Optics Letters, vol. 16, No. 4, pp. 273-275.

Qi, B., et al. (2003) "Novel data processing techniques for dispersive white light interferometer," Optical Engineering, vol. 42, No. 11, pp. 3165-3171.

Rao, Y., (2006) "Demodulation algorithm for spatial-frequency-division-multiplexed fiber-optic Fizeau strain sensor networks," Optics Letters, vol. 31, No. 6, pp. 700-702.

Rao, Y. (2006) "Recent progress in fiber-optic extrinsic Fabry-Perot interferometric sensors," Optic Fiber Technology, vol. 12, pp. 227-237.

Rao, Y., et al. (1993) "Design study of fibre-optic based Fabry-Perot type interferometric sensors using low-coherence signal recovery," Fibre Optic and Laser Sensors, vol. 2070, pp. 360-371.

Rao, Y., et al. (1996) "Recent progress in fibre optic low-coherence interferometry," Measurement Science Technology, vol. 7, pp. 981-999.

Rao, Y., et al. (2008) "In-line fiber Fabry-Perot refractive-index tip sensor based on endlessly photonic crystal fiber," Senors and Actuators A, vol. 148, pp. 33-38.

Rugar, H. J., et al. (1989) "Imporved fiber-optic interferometer for atomic force microscopy," Appl. Phys. Lett., vol. 55, No. 25, pp. 2589-2590.

Santos, J.L., et al. (1991) Passive demodulation of minature fiber-optic-based interferometric sensors using a time-multiplexing technique, Optics Letters, vol. 16, No. 15, pp. 1210-1212.

Schmidt, M., et al. (1999) "Fiber-optic extrinsic Fabry-Perot interferometer sensors with three-wavelength digital phase demodulation," Optics Letters, vol. 24, No. 9, pp. 599-601.

Schmidt, M., et al. (2001) "Fiber-Optic Extrinsic Fabry-Perot Interferometer Strain Sensor with < 50 pm displacement resolution using three-wavelength digital phase demodulation," Optics Express, vol. 8, No. 8, pp. 475-480.

Schmitt, J. (1999) "Optical Coherence Tomography (OCT): A Review," IEEE, vol. 5, No. 4, pp. 1205-1215.

Seaver, G. A. V. L. Vlasov, A. G. Kostianoy, (1997) "Laboratory Calibration in Distilled Water and Seawater of an Oceanographic Multichannel Interferometer-Refractometer," J. Atmos. Oceanic Technol. 14 (2), 267-277.

Sirkis, J., et al. (1995) "In-Line Fiber Etalon (ILFE) Fiber-Optic Strain Sensors," Journal of Lightwave Technology, vol. 13, No. 7, pp. 1256-1263.

Smith, D. T., et al. (2009) "A fiber-optic interferometer with subpicometer resolution for dc and low-frequency displacement measurement," Review of Scientific Instruments, vol. 80, pp. 1-8.

Tapia-Mercado, J., et al. (2001) "Precision and Sensitivity Optimization for White-Light Interferometric Fiber-Optic Sensors," Journal of Lightwave Technology, vol. 19, No. 1, pp. 70-74.

Tatsuno, K., et al.(1987) "Diode laser direct modulation heterodyne interferometer," Applied Optics, vol. 26, No. 1, pp. 37-40.

(56) References Cited

OTHER PUBLICATIONS

Urbanczyk, W., et al. (2001) "Digital demodulation system for low-coherence interferometric sensors based on highly birefringent fibers," Applied Optics, vol. 40, No. 36, pp. 6618-6625.

Velosa, E., et al. (2012) "Digital Control of a White Light Interrogtation System for Optical Fiber Interferometers," IEEE, vol. 12, No. 1, pp. 201-206.

Wang, A., et al. (2001) "Self-Calibrated Interferometric-Intensity-Based Optical Fiber Sensors," Journal of Lightwave Technology, vol. 19, No. 10, pp. 1495-1501.

Wang, T., et al. (1998) "A high precision displacement sensor using a low-finesse fiber-optic Fabry-Perot interferometer," Sensors and Actuators, vol. 69, pp. 134-138.

Wang, Z., et al. (2004) "Advanced iterative algorithm for phase extraction of randomly phase-shifted interferograms," Optics Letters, vol. 29, No. 14, pp. 1671-1673.

Webb, et al. (1988) "Extended-Range Interferometry Using a Coherence-Tuned, Synthesised Dual-Wavelength Technique With Multimode Fibre Links," Electronic Letters, vol. 24, No. 18, pp. 1173-1175.

Xu, J., et al. (2010) "Phase-shift extraction for phase-shifting interferometry by histogram of phase difference," Optics Express, Vo. 18, No. 23, pp. 24368-24378.

Yu, B., et al. (2006) "Analysis of Fiber Fabry-Perot Interferometric Sensors Using Low-Coherence Light Sources," Journal of Lightwave Technology, vol. 24, No. 4, pp. 1758-1767.

Yuan, L., (1997) "White-light interferometric fiber-optic strain sensor from three-peak-wavelength broadband LED source," Applied Optics, vol. 36, No. 25, pp. 6246-6250.

Zhang, G., et al. (2004) "An investigation of interference/intensity demodulated fiber-optic Fabry-Perot cavity sensor," Sensors and Actuators, vol. 116, pp. 33-38.

Zhang, Y., et al. (2010) "Fringe Visibility Enhanced Extrinsic Fabry-Perot Interferometer Using a Graded Index Fiber Collimator," vol. 2, No. 3, IEEE Photonics Journal, pp. 468-481.

Zhu, P., et al. (2012) "Single-shot two-dimensional surface measurement based on spectrally resolved white-light interferometry," Applied Optics, vol. 51, No. 21, pp. 4971-4975.

* cited by examiner

SUBMERSIBLE N-WAVELENGTH INTERROGATION SYSTEM AND METHOD FOR MULTIPLE WAVELENGTH INTERFEROMETERS

CROSS-REFERENCE TO RELATED APPLICATIONS

This application is related to and claims the benefit of priority to U.S. Provisional Application Ser. No. 61/757,465, entitled "N-Wavelength Interrogation System for Low Coherence Interferometers," filed on Jan. 28, 2013, and U.S. Non-Provisional application Ser. No. 14/166,650, entitled, N-Wavelength Interrogation System and Method for Multiple Wavelength Interferometers," filed Jan. 28, 2014, the entirety of which are hereby incorporated by reference. All publications cited herein including McDougall, T. J., D. R. Jackett, F. J. Millero, R. Pawlowicz, and P. M. Barker, 2012. A global algorithm for estimating Absolute Salinity. *Ocean Science*, 8, (6), 1123, McDougall, T. J. and P. M. Barker, 2011. *Getting started with TEOS-10 and the Gibbs Seawater (GSW) Oceanographic Toolbox*, Millard R. C., and G. Seaver, 1990. An index of refraction algorithm for seawater over temperature, pressure, salinity, density, and wavelength. *Deep-Sea Research* 37, 1909-1926, are incorporated by reference in entirety.

FIELD OF THE INVENTION

The present invention generally relates to interferometric measurements, and in particular to high resolution relative phase and absolute path length difference measurements for interferometric applications enabling improved combinations of resolution and range, which can be used for the determination of salinity, pressure, distance, and other physical and chemical parameters.

BACKGROUND

Interferometry makes use of superposition of electromagnetic waves with substantially the same frequency, to produce an interference pattern. Specifics of the interference pattern are due to the phase difference between the waves. Waves that are in phase undergo constructive interference while waves that are out of phase undergo destructive interference.

Typical interferometry methods, such as the well-known Michelson configuration, split a single incoming beam of coherent light into two substantially identical beams using a beam splitter such as a partially reflecting mirror. Each of the resultant beams is made to travel a different route, called a path. The two beams are then recombined at a detector. The difference in the path lengths traveled by each beam before reaching the detector creates a phase difference between beams, which can produce an interference pattern from the recombined beams. In general, any environmental condition encountered in the path of either or both beam(s) that alters the phase of the beam(s) (e.g., a change in the index of refraction of the path) prior to reaching the detector can produce an interference pattern and may impact the details thereof. Therefore, specific properties of the interference pattern can be assessed as indicators of any changes occurring along the path(s).

Very often, interference is detected using a spectrometer that separates wavelengths of light to produce a fringe pattern. Fringes are conventionally described as the light and dark bands produced by the interference of light. The regions of higher intensity (brighter bands) are generally caused by constructive superposition of the beams and the lower intensity (darker bands) regions are generally caused by destructive superposition. In the context of a graphical representation of intensity vs. wavelength (as depicted in FIG. 1A, for example) a fringe spectrum includes one or more fringe cycles. A fringe cycle can be described as a portion of the spectrum or corresponding waveform from one point of local maximum intensity e.g., the point "A" to the adjacent point of maximum intensity, e.g., point "B." The distance between these two points represents a full period of the fringe cycle. In general, a portion of the waveform corresponding to a fringe spectrum location between any two points on the waveform that are separated by one period and the intensity measurements corresponding to that waveform represent a full fringe cycle.

Interferometers generally measure an optical path length which is the product of physical distance and refractive index. As such, interferometers can be used to sense changes in either the physical distance or the refractive index. The term optical path length typically encompasses both refractive index and distance though, typically, only one may be varied and/or measured.

As described above, an absolute difference in light paths can generate an interference pattern also called a fringe pattern. As the absolute optical path difference changes, the fringe pattern also changes. The change in the fringe pattern can be periodic, i.e., the pattern repeats when the absolute path difference changes by one wavelength (e.g., by $\lambda_o$, which can be any one of the N wavelengths in the spectrum—e.g., the smallest, median, or the largest wavelength. A periodically changing fringe pattern can be called a fringe sequence.

Though the fringe pattern repeats, some associated parameter (e.g., fringe spacing) typically changes in a measurable way so that a fringe number m can be determined. The fringe spacing can be the spacing between adjacent peaks in the fringe spectrum. Techniques such as Fourier transform or linear fit can be used to compute an absolute path length difference and a corresponding fringe number and quadrant q. The absolute optical path length difference is approximately equal to $(m+q)\lambda_o$, where m is an integer and q is equal to 0, ¼, ½, or ¾.

Absolute measurement (frequency domain) techniques generally uses a spectrometer as the detector, and can be used to determine m and q described above. These techniques can provide a coarse estimate of the absolute optical path length difference, but the resolution to these techniques is low—typically no better than $\lambda_o/100$. Low-resolution relative phase techniques can be used as refinements to improve the resolution to as good as $\lambda_o/1000$. In these techniques, wavelength shifts of the spectral peaks are typically monitored and used to estimate path difference relative to a fringe. The resolution of these combined techniques, however, is still not as good as that of the highest-resolution relative phase techniques, which may have resolution as high as $\lambda_o/100,000$.

High-resolution relative phase techniques generally use three or more points/samples in a fringe spectrum. Traditionally in these techniques, these points/samples must be located in quadrature. Using these quadrature-spaced points, a high resolution relative measurement of the optical path difference, i.e., measurement of the optical path difference relative to a certain fringe, can be obtained. In other words, this technique can precisely determine φ such that the absolute optical path length difference is approximately equal to $(m+q+\phi/2\pi)\lambda_o$. But, alone, this technique does not determine m and q and, as such, does not provide information on absolute path length difference.

The high resolution relative phase technique discussed above also cannot be combined with the absolute measurement techniques, because the high resolution relative phase technique requires approximately quadrature-spaced points from the fringe spectrum. Absolute path length measurement techniques, however, often uses a spectrometer as the detector, which does not reliably provide approximately quadrature-spaced points. Instead, a spectrometer generally provides a fringe spectrum that includes only non-quadrature-spaced samples/points. To obtain the quadrature-spaced points, high resolution relative phase techniques typically employ some device other than a spectrometer, but then, absolute path length information cannot be readily obtained. In addition, these other devices are generally expensive and complex, which can significantly increase the cost and/or complexity of obtaining absolute optical path length difference measurements. Therefore, an improved system and method is needed to facilitate accurate high resolution absolute optical path length difference measurements in an efficient manner.

BRIEF DESCRIPTION OF THE DRAWINGS

Various embodiments of the present invention taught herein are illustrated by way of example, and not by way of limitation, in the figures of the accompanying drawings, in which.

SUMMARY OF THE INVENTION

Figure 1A:
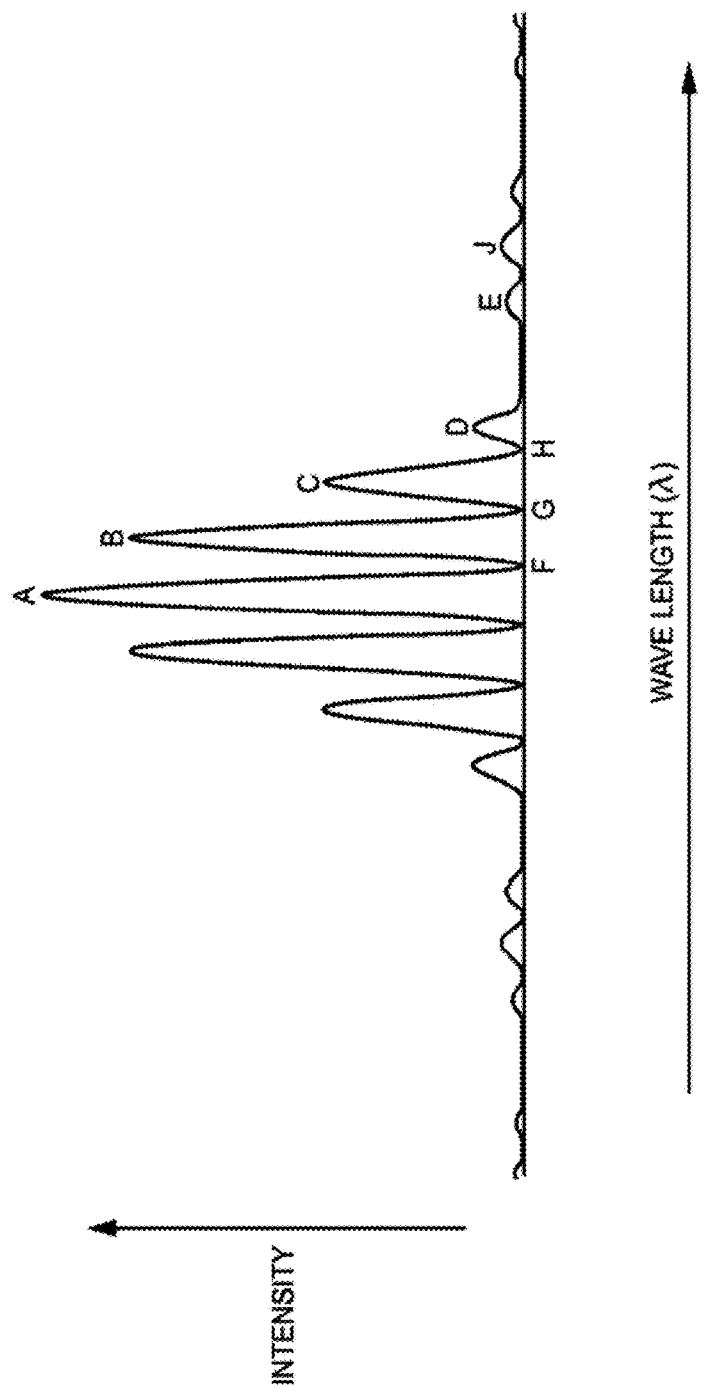
FIG. 1A schematically depicts a fringe spectrum.

Various embodiments described herein facilitate an efficient, high resolution absolute optical path length difference measurement. Specifically, the system and method applies novel analyses methods to interference patterns obtained from superimposed (combined) electromagnetic beams to precisely measure the absolute optical path length difference between the distance traveled by each beam from the point of beam splitting to the point of beam superposition. This is achieved, at least in part, by monitoring (also called interrogating) the intensity of the recombined beam at several specific wavelengths to obtain a fringe spectrum that includes one or more fringe cycles. When obtained using a conventional spectrometer, the fringe spectrum typically includes non-quadrature-spaced samples, as described below. Various properties of the fringe spectrum may be used to obtain a rough estimate of the absolute optical path length difference. A relative-phase measurement technique that can analyze non-quadrature-spaced intensity samples is used to analyze the same spectrum so as to determine a relative phase, i.e., a difference in the optical path lengths of the two beams relative to a fringe cycle, with high resolution.

Unlike other systems, the high resolution relative phase measurement is obtained from non-quadrature-spaced samples in the same spectrum that can be used to obtain a rough absolute estimate as well. Therefore, the rough estimate and the high-resolution relative phase measurement can be aggregated to provide a high resolution absolute optical path-difference measurement. Such a measurement based on monitoring the intensity changes of the non-quadrature-spaced samples may be limited only by the resolution of the analog to digital converter (ADC) used in analyzing the fringe spectrum. Since state of the art ADCs are readily available with resolutions above 1 part in 1,000,000, the various embodiments described herein can provide absolute optical path length difference measurement that have a resolution as high as $\lambda_0/100,000$.

This ability to determine the absolute difference in optical path lengths with extremely high resolution allows various embodiments to be used to perform highly precise measurements of a number of parameters of physical systems at heretofore unachievable combinations of range and resolution. Specifically, to the extent a parameter of a physical system of interest, such as an external force and/or an environmental condition associated with the system, and/or a change therein can produce an interference pattern, the measurement of the absolute path length difference enables determination of the parameter of interest within a broad range of magnitudes. As the measurement is performed at a high resolution using the same interference pattern, the determination of the parameter of interest not only can encompass a broad range of magnitudes but also can be performed with high precision.

Accordingly, a system is provided for measuring a parameter of interest in situ using a measurement of absolute optical path length difference. The system includes a radiation source adapted to emit electromagnetic radiation, a sample space exposed to an environmental condition and adapted to produce a fringe spectrum from the electromagnetic radiation, a detector capable of detecting the fringe spectrum, and an analysis system to receive the fringe spectrum from the detector. The analysis system derives a measurement of the absolute path length difference and uses the measurement to calculate a parameter of interest, and the system produces a high resolution absolute optical path length difference measurement of $\frac{1}{1,000}$-th up to $\frac{1}{100,000}$-th of a wavelength.

In one embodiment, the analysis system derives a measurement of the absolute path length difference based on the fringe spectrum, a base estimate of the absolute path length difference, a fringe number, a quadrant, and a relative phase measurement. The fringe spectrum further comprises two optical paths having an absolute optical path length difference therebetween that is to be measured. The fringe spectrum comprises a plurality of non-quadrature-spaced light intensity samples, each sample corresponding to a difference wavelength of light from a plurality of wavelengths, and the plurality of samples represents at least on full fringe cycle within the fringe spectrum. The base estimate is based on, at least in part, the fringe spectrum, and the quadrant is based on, at least in part, the base estimate and the selected reference wavelength. The relative phase measurement of the absolute optical path length difference is determined using the selected non-quadrature-spaced samples by expressing each light intensity sample as a combination comprising: (i) a term based on a relative phase $\varphi$ this is based on the reference wavelength and is independent of the monitored wavelengths, and (ii) a term based on a phase shift estimate $\delta_i(L)$ relating to both the monitored wavelength corresponding to the light intensity sample and the base estimate of the absolute optical path length difference.

In one embodiment, the analysis system further includes a receiver for receiving the fringe spectrum from the detector, a coarse estimator configured for selecting a reference wavelength from the various wavelengths. The coarse estimator is also configured to determine: (i) the base estimate of the absolute optical path length difference, based on, at least in part, the fringe spectrum, (ii) the fringe number and (iii) the quadrant based on, at least in part, the base estimate and the selected reference wavelength, and a sampler in communication with the receiver for selecting a set of non-quadrature-spaced samples from the plurality of samples. In addition, the system includes a relative phase estimator for determining the relative phase measurement of the absolute optical path length difference using the selected non-quadrature-spaced samples and an aggregator for deriving a measurement of the absolute optical path length difference by aggregating the relative phase measurement, the fringe number, and the quadrant.

The system may additionally include a transducer including a sensor which, in response to an environmental condition, is capable of altering either a physical path or a refractive index, or both of a path of radiation. A spectrometer coupled to the transducer may generate the fringe spectrum based on, at least in part, a radiation received through the path of radiation. The aggregator may be further configured to determine a parameter corresponding to the environmental condition using the measurement of the absolute optical path length difference.

The system may be employed to measure a parameter of interest selected from the group of salinity, pressure, density, temperature, strain, vibration, distance, refractive index of a medium, and changes thereof. According to one aspect of the present invention, the system is adapted to measure the parameter of interest in a body of water wherein the system may be operated at a depth of at least 1 m up to 6,000 m and in some embodiments, full ocean depth.

In one embodiment, the system may also include a radiation source adapted to emit at least N wavelengths of electromagnetic radiation, where N is at least equal to two. The radiation source may include a swept wavelength source, sweeping sequentially through the N wavelengths. In one embodiment, the radiation source includes a temperature and current stabilized 20 mW super-luminescent diode, having a wavelength centered at about 1061 nm and a full-width-half-maximum (FWHM) of about 33 nm.

In one embodiment, the system is adapted for use on a vehicle, a sampler, a profiler, an underwater observatory, and in a sensor array.

According to one embodiment, the system further comprises one of an optical switch, an optical filter, a dichroic filter, and a detector.

In another embodiment, the system also comprises a reference space in addition to the sample space which is adapted to produce a reference wavelength. The sample space comprises a sample path length of 5 mm or less, and in specific embodiments, approximately 1 mm.

DETAILED DESCRIPTION

Various embodiments evaluate the interference patterns produced by the recombination of two electromagnetic beams derived from a common radiation source, and that traveled unequal distances (path lengths) from the point of generation. Specifically, by evaluating the fringe spectrum intensities at multiple wavelengths across at least one full fringe cycle, phase shift and path length differentials may be calculated at a high resolution, e.g., up to $\frac{1}{100,000}$-th of a wavelength.

Various embodiments described herein take advantage of the characteristics of multiple wavelength techniques and provide a method that extends them to n selectively spaced wavelengths that are monitored via a spectrometer. This new n-wavelength technique can be combined with the absolute path length techniques without requiring any changes to be made to existing spectral detection setups. In some embodiments, the detector image is analyzed in the frequency domain in order to determine an initial fringe number and quadrant. For subsequent measurements, however, the image is analyzed for local relative phase by demodulating the n spectrometer wavelengths using a set of n simultaneous linear equations relating to n non-quadrature-spaced intensity measurements. The resulting combined method can preserve the resolution, speed, and simplicity of the multiple wavelength relative phase techniques and combines them with the range, stability, and absolute measurement capabilities of the absolute path length spectral domain techniques.

When a low coherence interferometer is interrogated with an n-element spectral detector, where each element monitors wavelength $\lambda_i$, the image can be characterized by $$I_i = A + \gamma_i B \cos(2\pi L/\lambda_i) \tag{1}$$

where $I_i$ is the intensity measured by each of the n detectors, A is the mean interferometric intensity, B is the interferometric fringe amplitude, L is the optical path length difference, and $\gamma_i$ is the modulus of the degree of first order coherence (The dc gain term and offset for each detector element has been omitted for now, for the convenience of explanation). Assuming a Doppler-broadened source, $\gamma_i$, can be estimated by $$\gamma_i = \exp\left[-\left(\frac{\pi L \Delta \lambda_i}{2\sqrt{\ln(2)}\,\lambda_i^2}\right)^2\right] \tag{2}$$

where $\Delta\lambda_i$ is the spectral FWHM received by each detection element.

In one embodiment, the first step in demodulating the set of image points for absolute path length is to determine the starting fringe number, m, as well as the starting fringe quadrant. This can be done by analyzing the spectral image in the frequency domain using one of a number of existing techniques. It is useful to note that in many cases this first measurement does not need to be performed fast, so averaging can be applied over multiple images to increase precision.

In one embodiment, once the initial fringe number and quadrant are determined, the n-wavelength interrogation technique based on non-quadrature-spaced intensity samples is used to perform high resolution, high speed relative phase measurements. To perform the relative phase measurements it is useful to re-write Equation (1) as $$I_i = A + \gamma_i B \cos(\phi + \delta_i) \tag{3}$$

where $\phi = 2\pi L/\lambda_o$, $\delta_i = 2\pi L[(\lambda_o - \lambda_i)/(\lambda_i \lambda_o)]$, and $\lambda_o$ is a known reference wavelength chosen from one of the $\lambda_i$ wavelengths. Expanding and re-writing Equation (3) yields $$I_i = A + \gamma_i C_1 \cos(\delta_i) - \gamma_i C_2 \sin(\delta_i) \tag{4}$$

where $C_1 = B\cos(\phi)$ and $C_2 = B\sin(\phi)$.

In some embodiments the responses for $\gamma_i(L)$ and $\delta_i(L)$ can be calibrated beforehand. In some embodiments, $\gamma_i$ and the associated terms can be omitted. The calibration of $\delta_i(L)$ involves determining $\lambda_i$, and can be done either by using a source with a known spectrum or by determining $\lambda_o$ and performing a calibration scan over the full interferometric range. The response for $\gamma_i(L)$ can also be determined by scanning the interferometer over its full range. Since $\gamma_i$ and $\delta_i$ vary slowly with respect to L, their initial values can be accurately estimated using the low resolution absolute path length measurement previously obtained. Now that $\gamma_i$ and $\delta_i$ are known quantities, Equation (4) becomes a set of n overdetermined linear equations that can be solved for the unknowns A, $C_1$, and $C_2$. After solving for these variables, the relative phase can be determined by realizing that $$\phi = a\tan(C_2/C_1) \tag{5}$$

This relative phase measurement only as to be adjusted with respect to the starting quadrant. The result can then be converted to an absolute path length using $$L = \lambda_o(m + \phi/2\pi) \tag{6}$$

In some embodiments, to improve the precision of $\gamma_i$, $\delta_i$, and L, Equations (4-6) can be iterated until a desired tolerance is reached. A similar approach is followed for subsequent measurements, however, instead of estimating $\gamma_i(L_t)$ and $\delta_i(L_t)$ using an absolute path length measurement, they can be initially estimated using the previous values $\gamma_i(L_{t-1})$ and $\delta_i(L_{t-1})$, where $L_t$ and $L_{t-1}$ are two consecutive measurements. For these subsequent measurements, fringe counting can be used to keep track of the total relative phase shift as long as the rate of change is less than n/measurement. This requirement also ensures that it is valid to use $L_{t-1}$ as a starting estimation for $\delta_i(L)$ and $\gamma_i(L)$. If the slew rate is faster, the absolute path length spectral domain method can once more be used to determine the fringe number and quadrant.

It is common for interferometers to simply measure an absolute path length, which typically means the difference between two arms of an interferometer, and in these cases it is ensured that the optical path length difference is within the system's coherence requirements. For example, if the system's coherence length, i.e., the maximum absolute path length difference for which the system can produce interference, is 0.25 mm, the system is typically constructed such that the absolute path length difference to be measured is much less than 0.25 mm. Various embodiments described herein, however, are configured to measure an optical path length that is longer than the system's coherence length. For example, in one embodiment, the system's coherence length is 0.25 mm, and the path length to be measured is roughly 20 mm. Therefore, a differential interferometer (often called a path-matching differential interferometer (PMDI)) can be constructed that measures the difference between two absolute path lengths. As described above, each absolute path length itself is a difference between two arms of one interferometer.

Using a PMDI, an interference pattern is obtained by maintaining the difference between the absolute path lengths to a value less than the system's coherence length. For example, in one embodiment, one optical path length is 20 mm and the second optical path length is maintained at 20 mm+0.25 mm. It should be understood the values described herein are exemplary, and that values of optical path length and absolute path length that are smaller or larger are contemplated. For example, the optical path length can be 10 mm, 15, mm, 25 mm, etc.

Figure 1B:
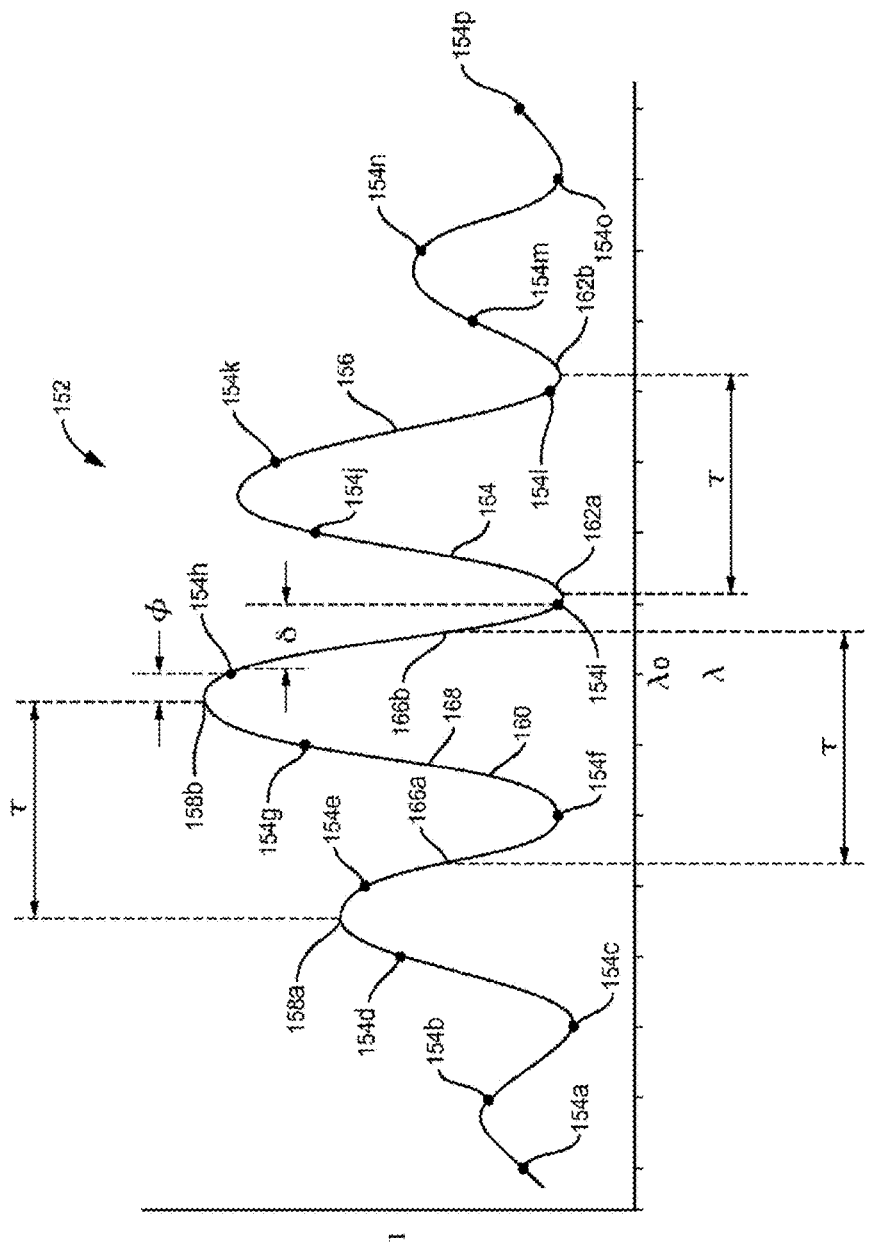
FIG. 1B depicts an exemplary fringe spectrum including non-quadrature-spaced samples.
Figure 2A:
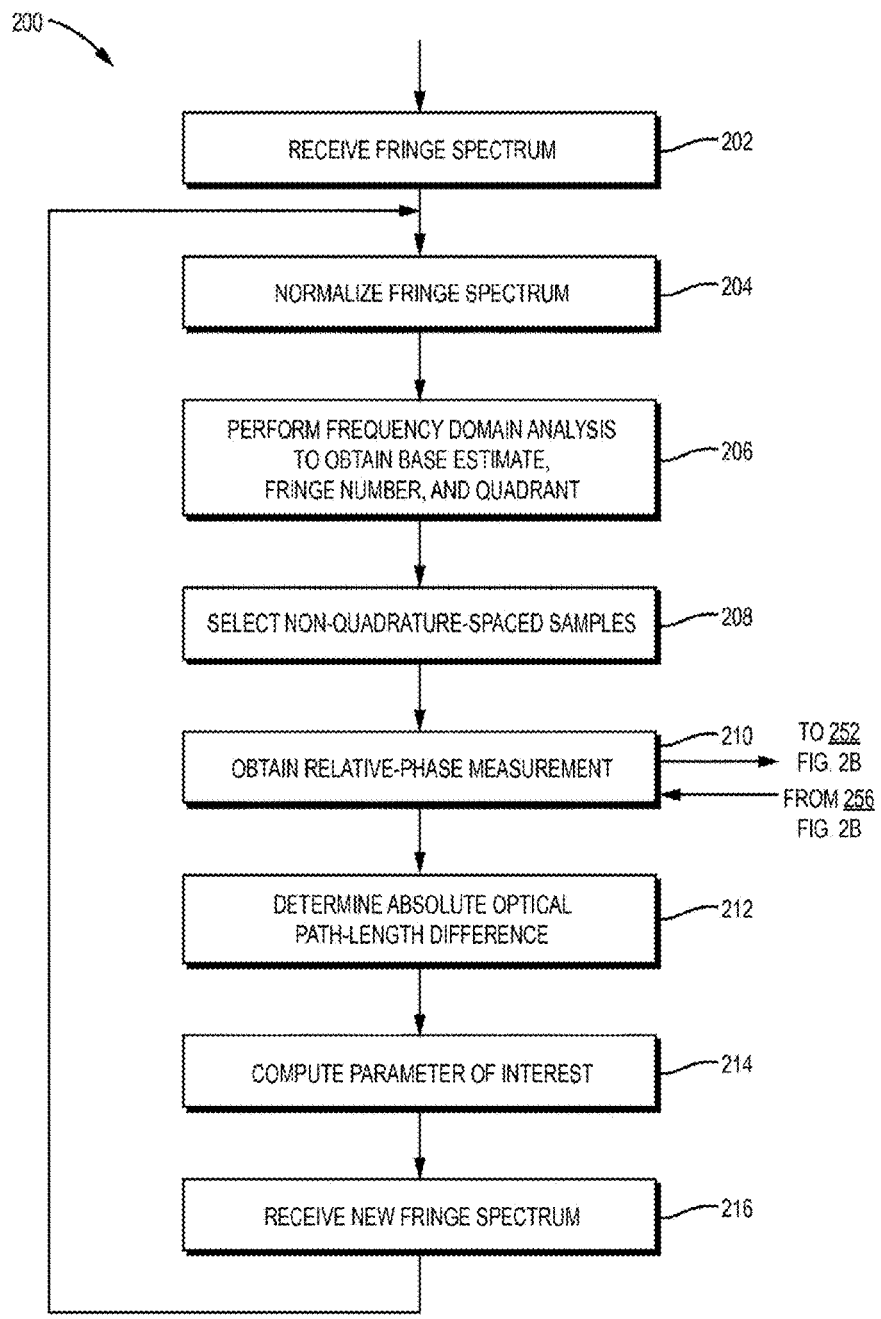
FIG. 2A illustrates a process of obtaining high resolution absolute optical path length different measurements, according to one embodiment.

With reference to FIGS. 1B and 2A, in a process 200 for obtaining a high resolution relative phase measurement of the absolute optical path length difference, a fringe spectrum 152 is received in step 202. The fringe spectrum, in general, may be produced by interference of two related beams of light, as described above, and may be supplied by a spectrometer. The fringe spectrum 152 includes several light intensity samples 154a-154q. Each sample corresponds to a different wavelength of light. A waveform relating intensities of the samples to the wavelengths thereof can be determined from the light intensity samples such that each sample substantially coincides with a unique point on the waveform. For example, the waveform 156 was derived from the samples 154a-154p. The waveform corresponding to a fringe spectrum generally includes one or more full fringe cycles.

A fringe cycle period is a distance between two adjacent local maximums (peaks) of the waveform corresponding to a fringe spectrum. The distance between two adjacent local minimums (valleys) is substantially the same as the distance between two adjacent peaks. A full fringe cycle typically includes a portion of the waveform and the corresponding samples between any two points on the waveform that are separated by a distance approximately equal to the fringe cycle period, along the wavelength axis.

To illustrate, points 158a, 158b represent adjacent peaks of the waveform 156. The distance between the peaks is τ and, as such, the fringe cycle period is τ. The portion of the waveform 156 between the peaks 158a, 158b is a full fringe cycle 160. The fringe cycle 160 includes the samples 154e, 154f, 154g. The points 162a, 162b represent adjacent valleys of the waveform 156, and the distance therebetween is also τ. As such, the portion of the waveform 156 between the valleys 162a, 162b is a different full fringe cycle 164. The fringe cycle 164 includes the samples 154j, 154k, 154l. The points 166a, 166b are neither peaks nor valleys, but these two points are separated by the fringe cycle period τ and, as such, the portion of the waveform 156 between the points 166a, 166b is also a full fringe cycle 168, which includes the samples 154f, 154g, 154h.

A full fringe cycle having a period τ can be divided into four quadrants respectively starting at distances 0, τ/4, τ/2, and τ/4 from the start of the fringe cycle. The phases corresponding to these quadrants are 0, π/2, π, and 3π/2, respectively. The samples separated in phase by approximately τ/4 are called quadrature-spaced samples and if any two consecutive samples in a set of samples is separated in phase by an amount different than τ/4, the samples in that set are called non-quadrature-spaced samples. A typical spectrometer usually provides non-quadrature samples. The fringe spectrum received in step 202 includes at least one full fringe cycle and at least one pair of non-quadrature-spaced samples. As such, the samples in the received fringe spectrum are non-quadrature-spaced. It should be understood that the fringe spectrum 152 is illustrative and that fringe spectrums that include as few as three and up to several thousand (e.g., 2,000, 5,000, 10,000) samples, one or more of which are non-quadrature samples, are within the scope of the present invention.

In an optional step 204, the received fringe spectrum (e.g., the spectrum 152) is normalized using known techniques, such as pre-calibration, Hilbert transform, etc. In normalization, generally the intensity of each sample corresponding to the spectrum is individually scaled such that in a waveform corresponding to the normalized spectrum all peaks have substantially the same intensities (e.g., +1) and all valleys have substantially the same intensities (e.g., −1). If the normalization method requires input parameters that are path length dependent, iteration may be used to improve the accuracy of normalization.

In another optional step 206, the spectrum (unmodified or normalized) is analyzed using a frequency-domain technique to obtain a coarse estimate (i.e., a base estimate) of the absolute optical path length difference. In addition, one of the wavelengths corresponding to the received spectrum (e.g., the spectrum 152) is selected as a reference wavelength. Often, the wavelength corresponding to the highest peak is selected as the reference wavelength. Using the base estimate and the selected reference wavelength, a fringe number m and a quadrant q are also computed in the step 206. These estimations and computations can be performed using known frequency-domain analysis techniques such as Fourier transform, peak detection, and different types of linear fits. It is useful to note that in many cases this first measurement does not need to be performed fast, so averaging can be applied over sample sets to increase precision. Alternatively, or in addition, other sensors or instruments can be used to estimate the absolute value of the measurement parameter to compute the estimate of absolute optical path length difference.

In step 208, a set of non-quadrature-spaced samples is selected from the samples in the received fringe spectrum. For example, the samples 154f, 154g, 154h, 154i may be selected, or the samples 154b-154m may be selected. If not selected in a previous step, a reference wavelength $\lambda_o$ is selected in the step 208. Using the selected non-quadrature-spaced samples and the reference wavelength, a high resolution relative phase measurement of the absolute optical path length difference is computed in step 210, as described below with reference to FIG. 2B. In an optional step 212, a high-resolution measurement of the absolute optical path length difference is obtained using the relative phase measurement, and the fringe number and the quadrant computed in the optional step 206 using, e.g., the expression L1=$\lambda_o$(m+q+(φ/2π)), where m is an integer and q can be 0, ¼, ½, ¾. In this expression, L1 is the high-resolution absolute path length difference measurement, $\lambda_o$ is the selected reference wavelength, m and q are the fringe number and the quadrant, respectively, and φ is the high resolution relative phase measurement.

In one embodiment, the computation of high-resolution relative phase measurement involves solving a system of equations. Each equation in the system corresponds to a different wavelength, denoted $\lambda_i$, in the received spectrum, and can represent the intensity of the corresponding sample as a function of a term based on the relative phase φ, and a term based on a phase shift estimate, denoted $\delta_i(L)$. The phase shift estimate can be expressed as $\delta_i(L)=2\pi L[(\lambda_o-\lambda_i)/(\lambda_o\lambda_i)]$ depends on both the wavelength $\lambda_i$ and the absolute optical path length difference L, which is to be measured. The phase shift estimate $\delta_i(L)$ can also be called a phase shift differential. If the wavelength corresponding to the sample 154h is selected as the reference wavelength, denoted $\lambda_o$ in FIG. 1B, the distance between the sample 154h and sample 154i, along the wavelength axis, represents the phase shift δ corresponding to the wavelength corresponding to the sample 154i. The distance between the sample 154h and the peak 158b of the corresponding fringe cycle represents the relative phase φ.

Figure 2B:
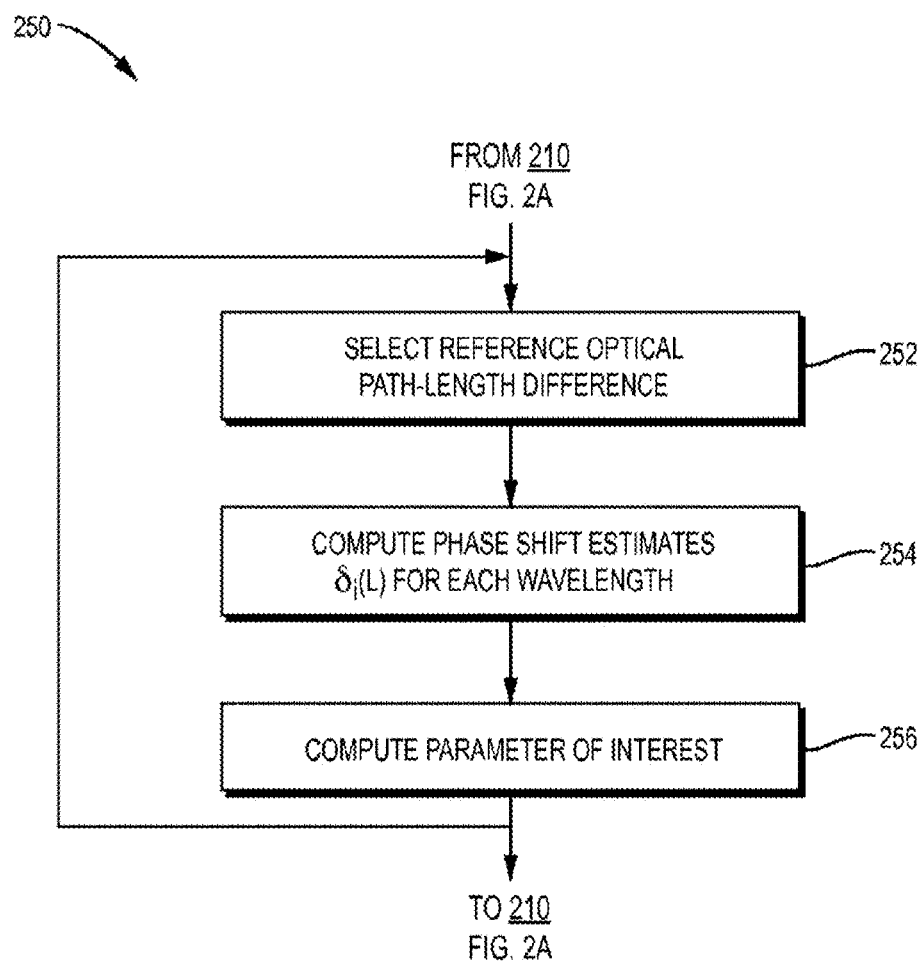
FIG. 2B illustrates a sub-process corresponding to one of the process steps illustrated in FIG. 2A.

With reference to FIG. 2B, in a process 250, a reference optical path length difference is selected in step 252 as described below, and the phase shift estimates $\delta_i(L)$ for each wavelength $\lambda_i$ are computed in step 254. The corresponding system of linear equations is solved in step 256 to obtain a high resolution relative phase measurement. The high-resolution measurement of the absolute optical path length difference computed in the optional step 212 can be used as the reference optical path length difference in the next iteration of the process 250. In any subsequent iterations, the measurement of the absolute optical path length difference computed in the optional step 212 of the previous iteration can be selected in the step 252 as the reference optical path length difference for that iteration.

As the absolute optical path length difference L is to be measured, the first time this computation is performed, the value of L is not known. As such, the base estimate of the absolute optical path length difference computed in step 256 is used as L. Thus, in the system of equations, the sample intensities and the phase-shift-based terms are known and the relative phase φ can be computed by solving the system of equations. The solution of the set of linear equations (e.g., Equation 4) may provide three values: an offset A, and two amplitudes $C_1$ and $C_2$. The two amplitudes can be used to calculate a measurement of the relative phase φ using Equation 5. Thereafter, in the optional step 212, a high-resolution measurement of the absolute optical path length difference L1 can be obtained using the relative phase measurement φ.

Recall, in the first iteration each phase shift estimate $\delta_i(L)$ corresponding to each wavelength $\lambda_i$ was computed using the base estimate. In some embodiments, when a high-resolution measurement of the absolute optical path length difference L1 is computed, that measurement is used to re-compute each phase shift estimate $\delta_i(L)$, as described above with reference to FIG. 2B. This can yield more accurate values of $\delta_i(L)$ because the value of L used in this iteration, L1, is generally more accurate than the base estimate. Using these more accurate values of $\delta_i(L)$, the equations can be solved again (i.e., the step 256 is repeated), to obtain a more accurate measurement of the relative phase φ. Thereafter, the step 212 may be repeated using the refined, more accurate measurement of the relative phase to obtain an updated, more accurate value L2 of the absolute optical path length difference. These steps may be repeated several times, as described with reference to FIG. 2B, so as to iteratively refine the values of $\delta_i(L)$, the relative phase measurement, and/or the measurement of the absolute optical path length difference.

The fringe spectrum received in the step 202 can represent an environmental condition related to parameters such as a certain salinity of a fluid (e.g., Absolute Salinity (TEOS-10; McDougall and Barker, 2011)), pressure, density, temperature, strain, vibration, location of an object, the refractive index of a medium (e.g., water, saltwater, freshwater, any fluid comprising an index of refraction), and changes in the values of any of these parameters, etc. The absolute optical path length difference computed using the fringe spectrum, thus relates to one or more of these parameters and to the environmental condition. Therefore, in an optional step 214, the measured absolute optical path length difference can be used to determine, e.g., to quantify the associated environmental condition. For example, using the measured absolute optical path length difference water temperature and/or salinity can be accurately estimated, pressure applied to an object can be determined, etc.

In some instances, when there is change in an environmental condition, the absolute difference between the two optical paths changes, generating a new spectrum. In an optional step 216, this new spectrum is received. Thereafter, one or more of the steps 202-212 are optionally repeated using the new spectrum. In one embodiment, only the steps 208, 210 are repeated, i.e., a base estimate based on the new spectrum is not computed. As such, in computing phase shift estimate $\delta_i(L)$ for solving the system of equations, the measurement of the absolute optical path length difference computed based on the previously received spectrum is used. By analyzing a change in the relative phase measurements corresponding to the new and the previous spectra the fringe number and/or quadrant increments or decrements can be determined. Specifically, if consecutive spectra are acquired fast enough, a typical change between relative phase measurements is less than $\pi/2$. When a fringe and/or quadrant changes, however, the change in the relative phase measurement is typically greater than $\pi/2$, resulting in a discontinuity in the optical path length measurements. This discontinuity can be corrected by incrementing or decrementing the fringe number in the step 212.

In solving the equations, the intensities associated with the new spectrum are used to obtain a new high resolution relative phase measurement. This new measurement and the previously computed fringe number and quadrant, adjusted if necessary as described above, are used to compute a new high resolution measurement of the absolute optical path length difference. As described above, the new high resolution measurement of the absolute optical path length difference can be iteratively refined. One of the advantages of this embodiment is that the step 206, which can be time consuming and/or costly, can be avoided in measuring the absolute optical path length difference corresponding to the new spectrum. This process can be repeated for additional fringe spectra corresponding to gradual changes in the parameter being measured. Thus, a parameter of interest can be efficiently tracked by performing the computationally expensive and/or slow frequency-domain analysis only once, and then repeating relative phase measurements as necessary.

Various embodiments can analyze any interference pattern produced by the super position of two or more related waveforms. In some embodiments the light used includes low coherence light, e.g., light that has a bandwidth ranging from about 10 nm up to about 400 nm in the ultraviolet, visible, or infrared regions of the electromagnetic spectrum. In another embodiment, the light source may be produced by overlapping three or more high coherence light beams at different wavelengths, which may increase system complexity and/or cost. In other embodiments, the light may be high coherence light with bandwidth less than 10 nm.

Beam splitting, which may occur more than once along the optical paths, may be accomplished by any suitable method (e.g., light may be split either by amplitude-division or wavefront-division). Exemplary beam splitting methods compatible with the various embodiments described above include, using a beam splitter, an optical fiber coupler, and/or a reflection from a metallic or dielectric surface, and/or using two axes of a birefringent fiber for subjecting two polarization axes of a single beam to two different indices of refraction. In some embodiments beam splitting is accomplished by a Fresnel reflection which occurs at the interface between the core of an optical fiber and a medium with a refractive index different than that of the fiber core.

Generally, any path geometry can be employed in the systems and methods described in various embodiments, as long as two paths have different optical path lengths. In some embodiments the optical paths include solid state paths (e.g., a path within an optical fiber or other light transmitting solid). In other embodiments, the path may be through a vacuum, air, or other suitable liquid or gaseous medium. Typically, one or more of the paths have either a variable physical length, or a variable index of refraction, or both.

Typically, an interference pattern is monitored using a detector capable of monitoring at least three wavelengths across at least one full fringe cycle. This can be accomplished using a spectrometer, or the individual components therein. In various embodiments, these components include wavelength separators such as a diffraction grating, a volume holographic grating, a prism, fiber optic or bulk optic filters, etc. The detector may include a photodiode, charge coupled device (CCD), or CMOS array of three or more detection elements, not necessarily arranged linearly. In some embodiments a low coherence source is scanned using a wavelength-tunable filter, and a single detector element (e.g., a photodiode) is used for detection. Another embodiment includes a tunable wavelength source and a single detector element.

In some embodiments, a spectrometer with a range of about 10 nm up to about 200 nm between wavelengths ranging from about 600 nm up to about 1600 nm is used. The spectral resolution of this embodiment can be between about 0.1 nm up to about 2 nm. In some embodiments, a superluminescent diode or LED between 100 nW and 1 W in output power is used as a light source. The wavelength specification of this source may match that of the spectrometer/detector, such that the various sets of wavelengths may have bandwidths varying between about 10 nm up to about 200 nm. The wavelengths may vary in the range from about 600 nm up to about 1600 nm.

The sample points (i.e., intensity measurements) to be selected from a received fringe spectrum for further analysis (e.g., relative phase measurement) can be determined by a processor receiving inputs from the detectors or by the detectors themselves. A typical number of points selected can range from 3 up to about 4096 pixels. In some embodiments, the intensity measurements/sample points are selected from at least one full fringe cycle. If more than one fringe cycles are available in the fringe spectrum, the spectrum may be sampled according to the Nyquist criterion i.e., at least two samples per fringe cycle are selected for subsequent analysis. A typical fringe spectrum includes from 2 up to 2000 fringe cycles. In general, in an interferometric system, the coherence properties of the light captured by any detector element influences the dynamic range of the system. Decreasing the bandwidth of the light on all the pixels can increases the dynamic range of the system.

Practical applications of the systems and methods described herein include the measurement of any parameter that can cause change in a physical distance and/or a refractive index including, physical distance, refractive index, atmospheric or hydrostatic pressure (P), density, temperature (T), sound pressure levels (SPL), vibration, strain, and chemical concentration (e.g., carbon dioxide, carbonate, nitrogen, alkalinity, silica) and composition. Each of the aforementioned employs at least one beam path which reproducibly changes the optical length thereof in response to changes in the corresponding parameter. As such, in various embodiments the beam paths are designed to change a physical length and/or index of refraction thereof in response to a physical parameter to be measured. The change in optical path length may occur as a direct effect of the parameter to be measured or a change therein, or via a transducer.

For accurate, reliable measurements of a parameter of interest, in various embodiments the path length is beneficially constructed to predictably vary in response to the parameter to be measured (e.g., pressure, temperature, etc.). In general, one or both path lengths may vary in response to the parameter being measured. To measure pressure and/or a change therein the deflection of a diaphragm or membrane due to applied pressure can be monitored. A change in birefringence of an optical fiber, a change in refractive index of a medium due to applied pressure, and/or the strain, e.g., change in size of a medium due to applied pressure may also be monitored.

In one embodiment, an optical fiber is placed opposite a reflective surface that moves in response to pressure, such as a diaphragm or membrane. In another embodiment, an optical fiber is placed within an optical cavity (e.g., sample space, sample cavity, sample volume, path, chamber, channel, space, opening) the length of which changes with pressure or other environmental condition or medium as described herein.

In one embodiment, a birefringent fiber is used to expose light to two refractive indexes that vary with pressure. To measure strain, an optical fiber can be placed within an optical cavity the length of which changes with strain. Alternatively or in addition, an optical cavity may be generated within an optical fiber, such that the length of the cavity changes with strain, so as to measure the strain and/or changes therein.

To measure temperature and/or changes therein the change in refractive index of a medium due to temperature and/or the strain, e.g., change in size of a medium due to temperature can be measured. As such, an optical fiber may be placed within an optical cavity the length of which can change with temperature. Alternatively, or in addition, an optical cavity may be generated within an optical fiber, such that the length of the cavity changes with temperature, so as to measure the temperature and/or changes therein.

In some embodiments, change in the refractive index of a solid, liquid, or gas, due to changing chemical composition thereof are monitored. To this end, in one embodiment, to measure a refractive index of a medium and/or a change therein, an optical fiber is located opposite from a mirror such that light exits the fiber, travels through the medium, reflects off the mirror, travels through the sample again, and re-enters the fiber. To measure vibration, in one embodiment an optical fiber is placed opposite a reflective cantilever or surface that undergoes vibration. In some embodiments, an optical fiber is placed opposite a reflective surface, and the distance between the fiber tip and the mirror is monitored.

In some embodiments, the system comprises one optical cavity (e.g., sample space) wherein light within the space may be altered when exposed to an environmental condition, changing the optical path length of the light. In further embodiments, the system comprises one or more optical cavities of which one or more cavities are exposed to an environmental condition and/or one or more cavities are not exposed to the environmental condition referred to as reference cavities. A reference cavity is typically unaltered and provides a reference wavelength of which can be used in the inventive method described herein.

The optical cavity is generally of a length less than 10 mm, 10 mm to 5 mm, 5 mm to 1 mm, 1 mm, or 200 μm or less. In some embodiments, the path length is approximately 1 mm which allows the elimination of the need for a grin collimator to be able to collect a sufficient amount of light returned from the reflective surface within the optical cavity.

Practical applications of the system and method include use in an aquatic environment. In some embodiments, the system is capable of measuring a parameter of interest in a body of water such as the ocean, a lake, a pond, an estuary, or other water source. In general, the system is capable of operating at a depth of at least 1 m, but in many cases, the system is adapted for use in deeper waters up to 100 m, 6,000 m, and even full ocean depth (about 11,000 m).

Figure 3:
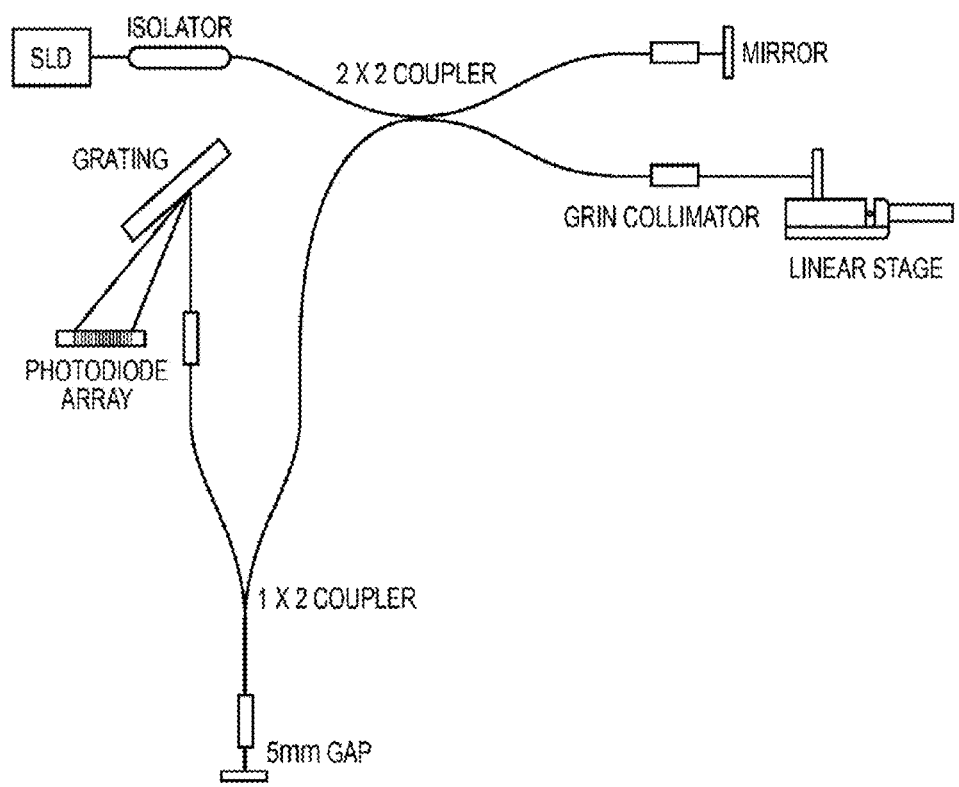
FIG. 3 schematically depicts a measurement and calibration system, according to one embodiment.

The n-wavelength interrogation technique was demonstrated using an embodiment using a fiber optic path-matching interferometer that was designed to perform high resolution refractive index measurements in a 5 mm sample cavity as depicted in FIG. 3. However, in order to demonstrate the n-wavelength interrogation technique, it was more practical to use the system not as a refractive index sensor, but instead, as a displacement sensor that monitored the position, D, of the linear stage, where D=L/2, and L is the difference in optical path length differences between the Michelson-style sensing interferometer and the Fabry-Perot-style receiving interferometer, which for this experiment, contained air of constant refractive index. The Michelson sensing interferometer was formed using a 2×2 polarization maintaining coupler with grin collimators at both outputs. One arm of the Michelson sensing interferometer was placed opposite a fixed mirror, and the other was placed opposite a mirror mounted to a motorized linear stage. The Fabry-Perot receiving interferometer was formed using a 1×2 PM coupler also with a grin collimator at the output. To create the reference reflection for the receiving cavity, the fiber end was polished flat resulting in a 4% reference reflection at the air gap just behind the grin lens. To equalize the intensity of the reference and the mirror-returned reflections, the length of the grin lens was adjusted slightly by polishing to reduce the coupling efficiency of the mirror-returned reflection until it matched the intensity of the reference reflection.

The source was a temperature and current stabilized 20 mW superluminescent diode centered at 1061 nm, and it had a FWHM of 33 nm. The detector was a simple spectrometer created using a 1500 lines/mm grating to diffract the 33 nm bandwidth evenly over a 16 element Si photodiode array. For this system, n was intentionally chosen to be low to optimize for resolution over a short range. The spectral width received by each detection element was approximately 2.2 nm, and this theoretically results in a 95 um working range with less than 50% signal attenuation that is between 17 um<D<112 um. The 16 signals were digitized using a 20-bit ADC at a rate of 1 kHz. All fiber in the system was polarization maintaining in order to maximize stability as well as grating efficiency.

Figure 4:
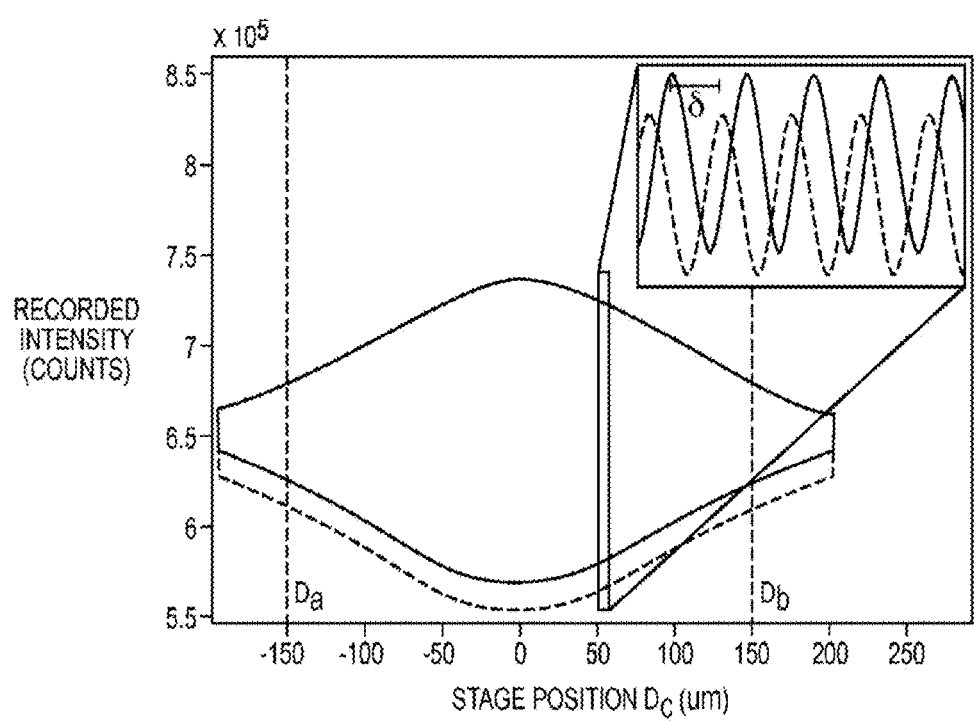
FIG. 4 depicts a calibration scan, according to one embodiment.

During this experiment the response of each detection element was characterized by $$I_i = G_i[A + \gamma_i B \cos(2\pi\lambda_i/L)] + b_i \quad (7)$$

which is similar to Equation (1) with the addition of constants $G_i$ and $b_i$ to respectively account for the gain and dark offset of each detection element. To determine $b_i$, a dark spectrum was acquired while the SLD was not powered. In order to determine $G_i$, $\gamma_i$ and $\lambda_i$ a calibration was performed by scanning the stage over a distance of about 400 um across D=0. FIG. 4 shows the intensity recorded for two of the 16 detection elements during the calibration scan. Initially, the position of the stage during the calibration scan, $D_c$, was not accurately known since the stage motion was not completely smooth. So it was first necessary to select the reference signal, $I_o$, and determine its corresponding wavelength, $\lambda_o$, to use in subsequently determining $L_c$. This was done by first calculating $G_i$ from the DC offset of each signal after $b_i$ was subtracted out. Then we selected $I_o$ to be the signal with the highest gain, and for it to correspond to the SLD's peak wavelength of 1065 nm. Next, that signal's zero crossings with respect to the central fringe were counted to generate $D_c$.

Once $D_c$ was determined, $\gamma_i(D_c)$ was determined by measuring the fringe amplitude as a function of $D_c$ for each signal using consecutive maxima and minima. Finally, $\lambda_i$ was calibrated by calculating the total relative phase shift, $\Delta\emptyset_{ab}$, of all the signals at two randomly selected positions $D_a$ and $D_b$, that were widely spaced on either side of the central fringe and using the relation $$\frac{\lambda i}{\Delta D} = 2\pi/\Delta\emptyset_{ab} \quad (8)$$

Rather than using $\Delta D = \Delta D_{ab}$ to calculate $\lambda_i$, $\Delta D$ was set to 1, and the result was normalized by requiring that $\lambda_i = \lambda_o$ for signal $I_o$. It was also possible to repeat this calculation for numerous points a and b to increase the precision of $\lambda_i$.

In one embodiment, the interferometer uses an illumination source that emits and receives N (e.g., 16, 32, etc.) wavelengths simultaneously. The intensity of the N wavelengths is acquired simultaneously by N detector elements, and the linear equation processing is performed on the acquired N samples. In other embodiments, a swept wavelength system uses a source that emits only one wavelength at a time, but the wavelength can be varied at different times. As such, this system acquires the N samples by varying the wavelength through N different wavelengths at different times, and by using only one photodiode to record N samples at N points in time. Those samples are then processed together, as described above.

Figure 5A:
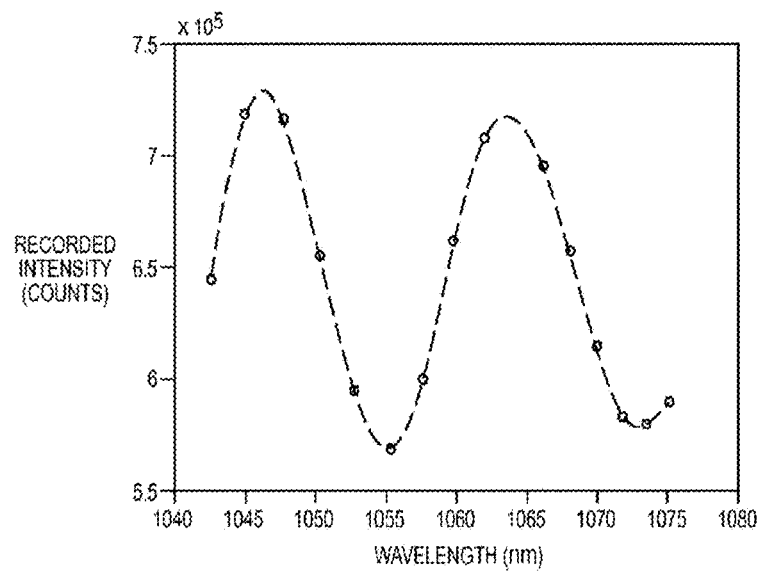
FIGS. 5A-5B depict a fringe spectrum and related waveforms, according to one embodiment.

After the calibration parameters were determined, the initial position of the interferometer was actively set by moving the mirror on the linear stage so that D was within the system's working range. FIG. 5A shows the detector image recorded at this starting position. The image in the figure is corrected for $G_i$ and $b_i$ but not $\gamma_i$. Next, the fringe number and quadrant for the initial position were determined by performing an absolute path length calculation on the spectral image. As previously indicated, there are a number of existing methods that can be used for this step, and the robustness of each method is sensitive to both n and the number of fringes in the image. Accordingly, several methods were tested beforehand, and the method described by proved to be the most robust for our setup, resulting in a typical error of ±1 fringe. It should be noted that the accuracy with which the initial position can be determined increases significantly for systems with higher n and for starting positions with more fringes.

Figure 5B:
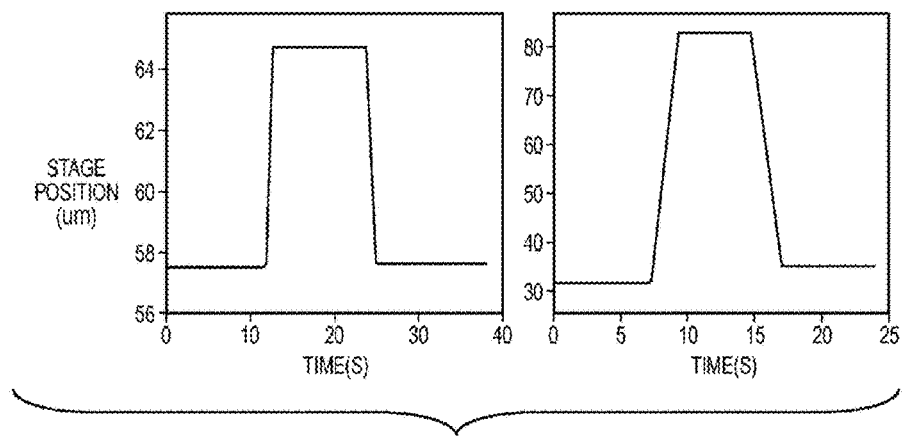
Figure 6:
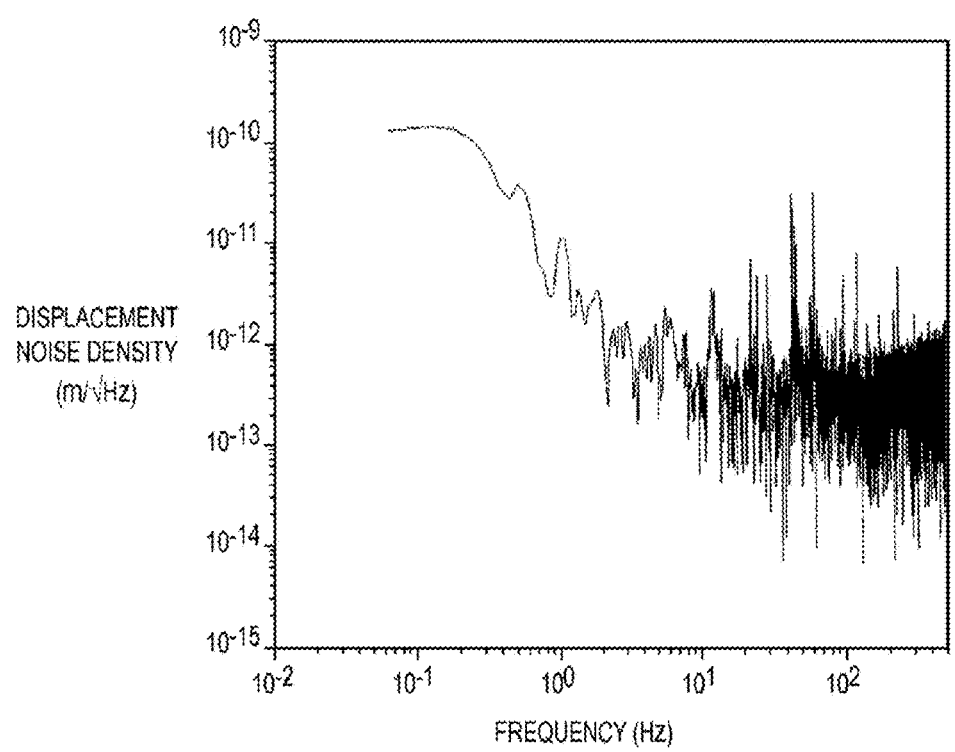
FIG. 6 depicts a calibration waveform, according to one embodiment.

After the initial position had been determined, a short 10 μm/s move was performed with an acquisition rate of 1 kHz, and the new interrogation method was used demodulate the signal. The full process, including resetting the starting position, was also repeated a second time for longer move. The two moves were intended to be 10 um and 50 um, respectively, but since the stage was not backlash compensated, the resulting forward motions were roughly 7 um and 51 um respectively. FIG. 5B shows the results of these moves, and they indicate that the system can achieve high resolution over a large dynamic range. FIG. 6 shows the power spectrum density (PSD) of the stable signal corresponding to the first 10 seconds of the 7 um move, and it indicates that the noise floor of the system is better than 0.5 pm/Hz$^{-1/2}$. When summed over the 500 Hz Nyquist bandwidth, this results in a total noise amplitude of 11 pm. This noise figure approaches the shot noise limit for the detected power (roughly 250 nW per detector element) as well as the analog-to-digital (ADC) quantization noise limit, which together result in a displacement noise of about 0.15 pm/Hz$^{-1/2}$.

The working range of the described embodiment is 95 um with 50 percent attenuation, and accordingly the noise figure indicates a range to resolution ratio of better than 8×10$^6$. It is also worthwhile noting that this ratio could be improved considerably by using a detector with more elements, each receiving a smaller spectral bandwidth. For a 1024-element spectrometer as the detector, each element would receive a spectral width of approximately 0.03 nm, and this would extend the 50 percent attenuation limit to just over 8 mm. Of course the resolution would decrease by a factor of (1024116)$^{1/2}$ to 176 pm, but this would still result in a range to resolution ratio of around 4×10$^7$. This could theoretically be improved even further by using a stronger source, or by using an interferometric setup with lower loss.

When compared to previous relative phase interrogation methods, the systems and methods described herein provide the advantages of high resolution, and high speed, and they do so while considerably expanding the working range. They also alleviates the need to precisely tune to quadrature. In terms of the method's absolute measurement capabilities, it greatly enhances resolution when compared to previous absolute path length methods, and in cases for which the initial fringe position is determined with sufficient accuracy, the systems and methods exhibit both high resolution and high accuracy. In addition, this technique is not limited to low coherence interferometers, and is applicable to any interferometer using a multiple wavelength source.

Figure 7:
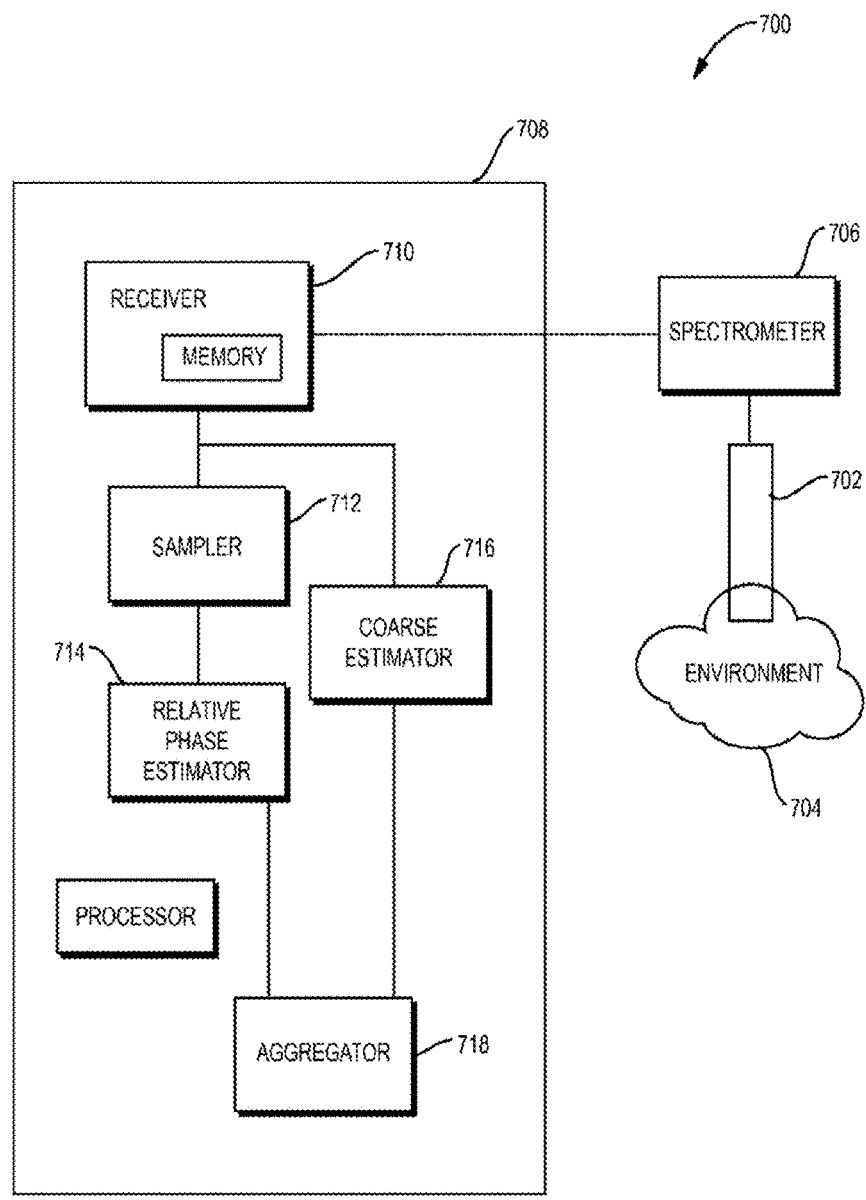
FIG. 7 schematically depicts an absolute optical path length difference measurement system, according to one embodiment.

With reference to FIG. 7, a transducer 702 (such a pressure, temperature, salinity, sensor) may sense a condition (e.g., salinity, pressure, temperature, strain, vibration, distance, refractive index of a medium, and changes thereof) of an environment 704. In response, the transducer 702 may alter either a physical path or radiation, a refractive index, or both. In response, the spectrometer 706 may generate an interference pattern and provide a fringe spectrum to the analysis system 708. The receiver 710 can store and/or supply the spectrum to a sampler 712. The sampler 712 may select a set of non-quadrature-spaced samples, and the relative phase estimator 714 can compute a relative phase measurement using the selected samples. The coarse estimator 716 can generate an absolute optical path length difference estimate of the change in the optical path introduced by the transducer 702, and a fringe number and quadrant corresponding to that estimate. The aggregator 718 may combine the fringe number, the quadrant, and the relative phase measurement to provide a high resolution measurement of the absolute optical path length difference.

Analysis system 708 comprises a receiver 710, a sampler 712, a coarse estimator 716, a relative phase estimator 714, and an aggregator 718. Receiver 710 receives a fringe spectrum comprising a plurality of light intensity samples from the detector (e.g., spectrometer 706). Sampler 712 in communication with the receiver selects a set of non-quadrature-spaced samples further comprising a plurality of wavelengths from the plurality of samples. From the plurality of wavelengths, coarse estimator 716 is configured for selecting a reference wavelength in the plurality of wavelengths and determining a base estimate, a fringe number, and a quadrant. Relative phase estimator 714 then determines the relative phase measurement of the absolute optical path length difference using the selected non-quadrature-spaced samples. Aggregator 718 aggregates the relative phase measurement, the fringe number, and the quadrant to derive a measurement of the absolute optical path length difference. The measurement of absolute optical path length difference is then used to calculate a measurement of a parameter of interest. Transducer 702 in response to an environmental condition alters at least one of a physical path and a refractive index of a path of radiation.

Exemplification

Described below is one embodiment of the present invention applied as a sensor for the measurement of absolute salinity.

A new optical system is described to make direct measurements of the index of refraction and thus the Absolute Salinity and density of a body of water (e.g., seawater) without using its electrical conductivity. The technology employs a novel type of interferometer that uses a spectrum of wavelengths and a new interrogation scheme that leads to high sensitivity, wide range, and high accuracy. Recent work on the seawater Equation of State by the SCOR Working Group 127 (McDougall et al, 2012) has resulted in a new Thermodynamic Equation of State (TEOS-10; McDougall and Barker, 2011) and notes the deficiencies in the traditional conductivity-based Practical Salinity, recommending a transition to Absolute Salinity. This differs from Practical Salinity due to the variations in constituents, especially in silicates, which do not affect electrical conductivity but do affect salinity and density. However, the only way suggested to estimate the Absolute Salinity is to infer it from geographic location and documented variations in the non-conducting elements. The described system would allow its direct in situ measurement. Also, since index of refraction corresponds much more closely to density than conductivity, improvements in the accuracy of density profiling are achieved. The sample volume of the system is small, and sampling can be performed fast, thus providing the capacity for both high resolution and high speed sampling if desired for mixing studies, while retaining the ability to make high accuracy salinity and density determinations.

This system utilizes advancements in fiber optic technology and high capacity field programmable gate arrays (FPGA) to produce a new family of oceanographic sensors around the disclosed novel interrogation scheme. Furthermore, the system enables direct measurements of Absolute Salinity and higher resolution salinity and density profiles. Salinity is now recognized as an important indicator of the changing global water cycle and promises to be useful in seasonal rainfall predictions, thus expanded salinity sampling tools are of direct benefit to society. The present technology also has applications in the medical, food, and chemical processing industries.

The in situ sensor system for the index of refraction provides a new way of measuring salinity and density profiles in a body of water (e.g., in the ocean). The measurements are made using a new high resolution optical interferometer capable of measuring and monitoring refractive index. While the system allows for the measurement of Absolute Salinity, it may be combined with the traditional CTD (conductivity, temperature, depth) device (or other water samplers) for utility in monitoring chemical properties such as nutrients, carbon dioxide, pressure, etc. Water samplers, as known in the art, are generally used to collect one or more samples of the surrounding aquatic environment for analysis in the laboratory setting. The system can also be used or integrated with traditional wire-lowered profiling systems (i.e., profilers) which measure parameters of interest as they travel though the water column such as dissolved oxygen, pH, fluorescence, pressure, etc. Other compatible systems which may use the present invention include underwater vehicles (e.g., autonomous underwater vehicles (AUVs), remotely operated vehicles (ROVs), submarines, floats, gliders, and the like), moorings, underwater observatories, sensor arrays, among other applications as known in the art. The present invention may also be used as a stand-alone device.

Oceanographers routinely deploy instruments to measure the temperature and conductivity of water body and thereby compute its salinity and density. These measurements play important roles in a number of areas, some of which include ocean circulation, stratification, nutrient transport, heat content and heat transport, acidification, and carbon sequestration. The existing CTD technology in broadest use has changed little in the last four decades. This new system provides an alternative to the standard CTD approach by measuring the optical refractive index, a parameter that is closely related to density and is based on an innovative multi-wavelength interferometric technology disclosed herein that provides unprecedented resolution and sensitivity. Because of its close correspondence with density, it provides a method for determining the Absolute Salinity as an alternative to conductivity-based Practical Salinity.

Figure 8A:
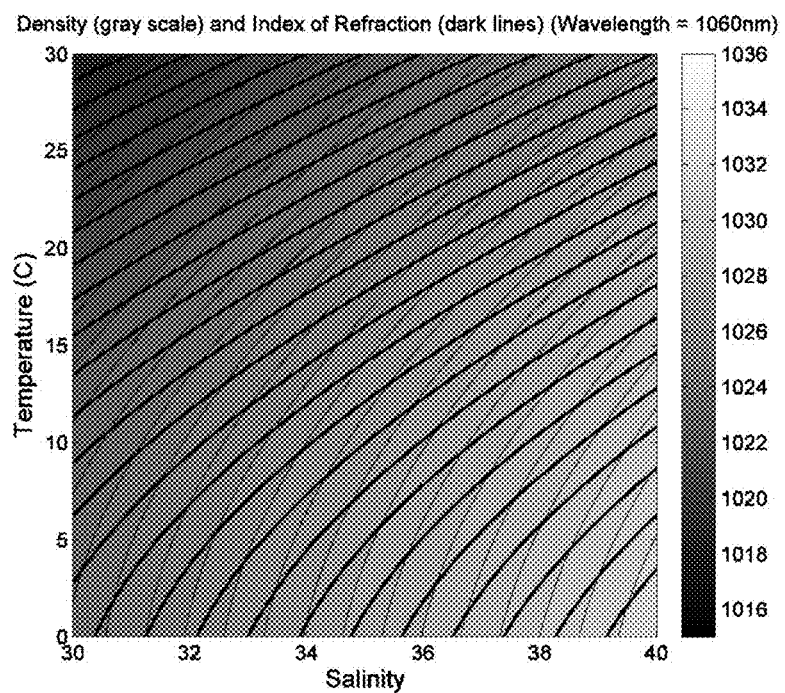
FIG. 8A depicts color contours of seawater density with lines of constant index of refraction over the oceanic range of temperature and salinity. (Standard Seawater of S=35, T=15 lies directly in the center). Both density and index increase to the lower right. The change in density over this range at zero pressure amounts to about 1.4%, the change in index about 0.34%. Over the full range of ocean pressures the percentage variations are about 3 times larger for each.
Figure 8B:
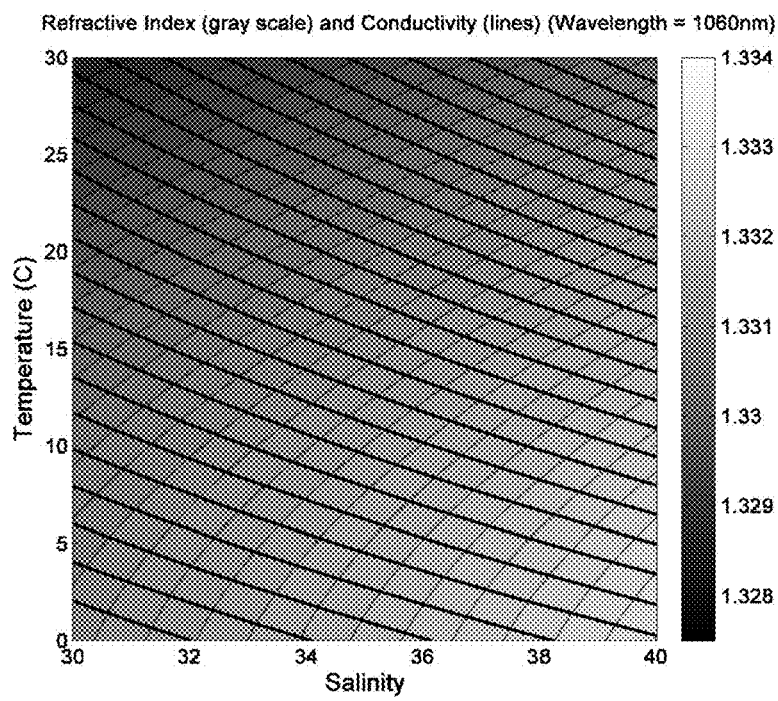
FIG. 8B depicts color contours of index of refraction overlain with lines of constant electrical conductivity. The conductivity increases to the top right of the diagram, whereas index increases to the lower right. Conductivity is proportional to the sum of T and S and index proportional to the difference of T and S. Thus, conductivity is like "spice" and index is like density, with the two being approximately orthogonal in the T-S plane (depending on choice of scales)

The refractive index of seawater has a distinctly different dependence on temperature and salinity than electrical conductivity. Like density, it is related to the difference of temperature and salinity, in contrast to conductivity which is proportional to the sum of temperature and salinity. FIG. 8 illustrates the differences over the oceanic range of salinity and temperature. The optical index of refraction of seawater varies closely with the in situ density (FIG. 8A). This dependence on density means that it has a significant pressure dependence and that the contributions from temperature and salinity tend to cancel one another. That is, in the T-S plane, lines of constant index tend to slope upward with increasing salinity (the index is proportional to the difference of T and S). This is in distinct contrast with the electrical conductivity of seawater (proportional to the sum of T and S), where the isolines slope downward with increasing S (FIG. 8B). The variable orthogonal to density in the T-S plane is often termed "spice" (high spice=hot and salty). Conductivity most closely corresponds to spice whereas optical index more closely corresponds to density. Conductivity is thus distinctly less useful for density measurement, and must always be paired with temperature. This "orthogonality" condition for index and conductivity offers an intriguing possibility for water mass discrimination, as it would provide a means of distinguishing water masses of different origin, since there are known variations in the ratios of ionic constituents that introduce errors in the conductivity based practical salinity currently used. These are related to nutrients (silica) and the carbon dioxide concentration and alkalinity, raising the potential for the index measurement to provide new insight into the chemical as well as the physical state of the ocean. This will allow the direct measurement of the new "Absolute Salinity", rather than its inference from geographical location.

This new approach utilizes a low-coherence interferometer to monitor refractive index by measuring the optical path length of a sensing space (e.g., sample space, optical cavity) exposed to the fluid sample. To acquire and process the interference signal, a new multiple wavelength interrogation scheme paired with a miniature spectrometer monitors the interference pattern. The intensity of each of the 'n' monitored wavelengths is demodulated for relative phase using a set of 'n' simultaneous linear equations. The technique provides high resolution relative phase measurements that can be easily integrated with existing lower resolution techniques that measure absolute path length. The combined result is a high resolution absolute refractive index measurement that is robust, high speed, and has large dynamic range.

Figures 9A, 9B, 9C:
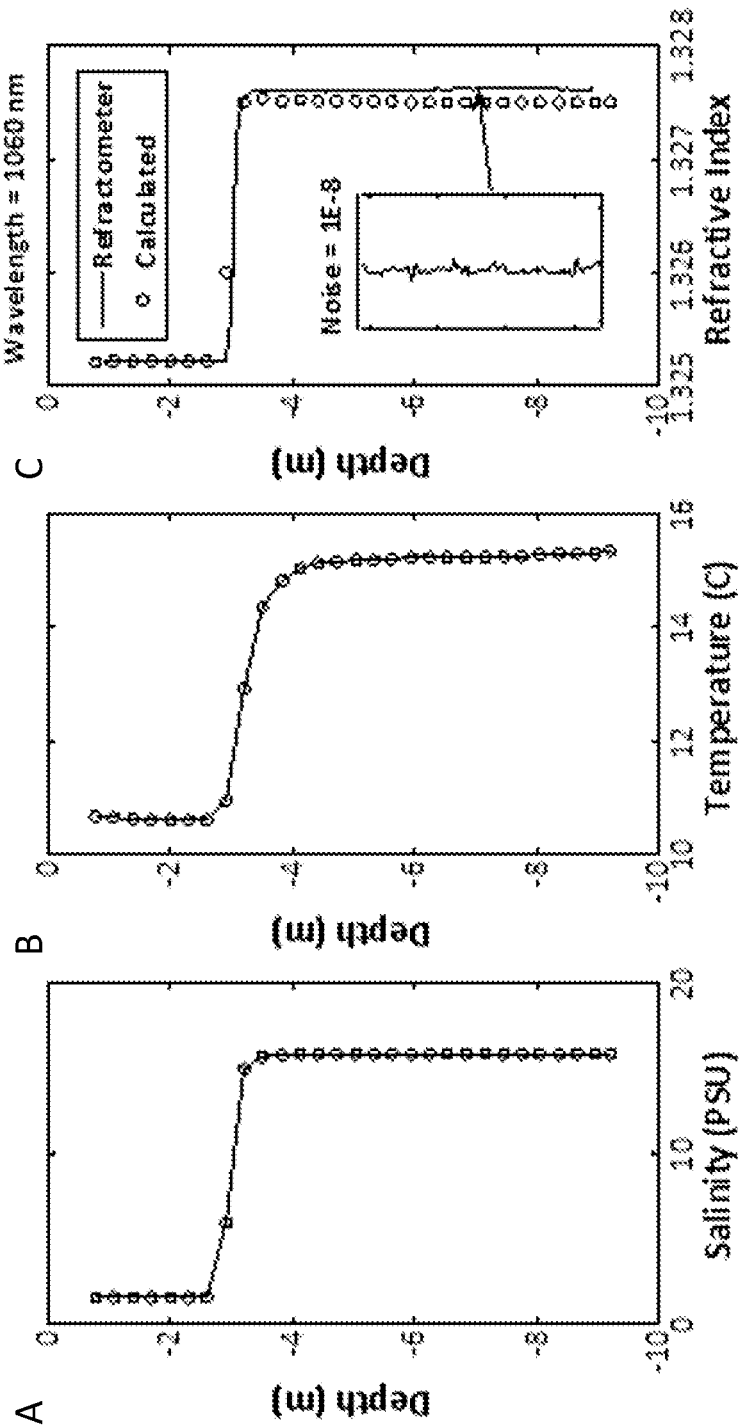
FIGS. 9A-9C illustrates the vertical profiles of salinity (A), temperature (B), and index of refraction (C) in a 10 m laboratory tank. S and T are from a Castaway CTD sensor. They are used in the Millard and Seaver (1990) formula for the index of refraction to calculate the blue curve in the third panel. The measured output of the refractometer is shown in the black curve. It has higher spatial resolution than the CT sensor (~1 mm versus 30 cm) and a noise of approximately $1\times10^{-8}$. Note: the wavelength of 1060 nm is outside the calibration range of the Millard and Seaver formula.

The instrument was meticulously designed to measure in situ refractive index with high resolution, high stability, a wide operating range, and a fast sampling speed. Experimental results showed that the present interrogation method can measure refractive index over the full range of seawater with a resolution of $1 \times 10^{-8}$. This is equivalent to measuring the variation in water's refractive index due to a 60 ppb change in salinity, a $1 \times 10^{-4}$° C. change in temperature, or a $6 \times 10^{-3}$ dbar change in pressure (FIG. 9A-9C). The dynamic range of the system is approximately $10^7$, and the sample rate can be set as high as 1 kHz. In some embodiments, the sample rate is at least 0.1 Hz, at least 1 Hz, at least 10 Hz, at least 100 Hz, at least 1 kHz, at least 10 kHz, up to 10 kHz, and up to 100 kHz.

Figure 10:
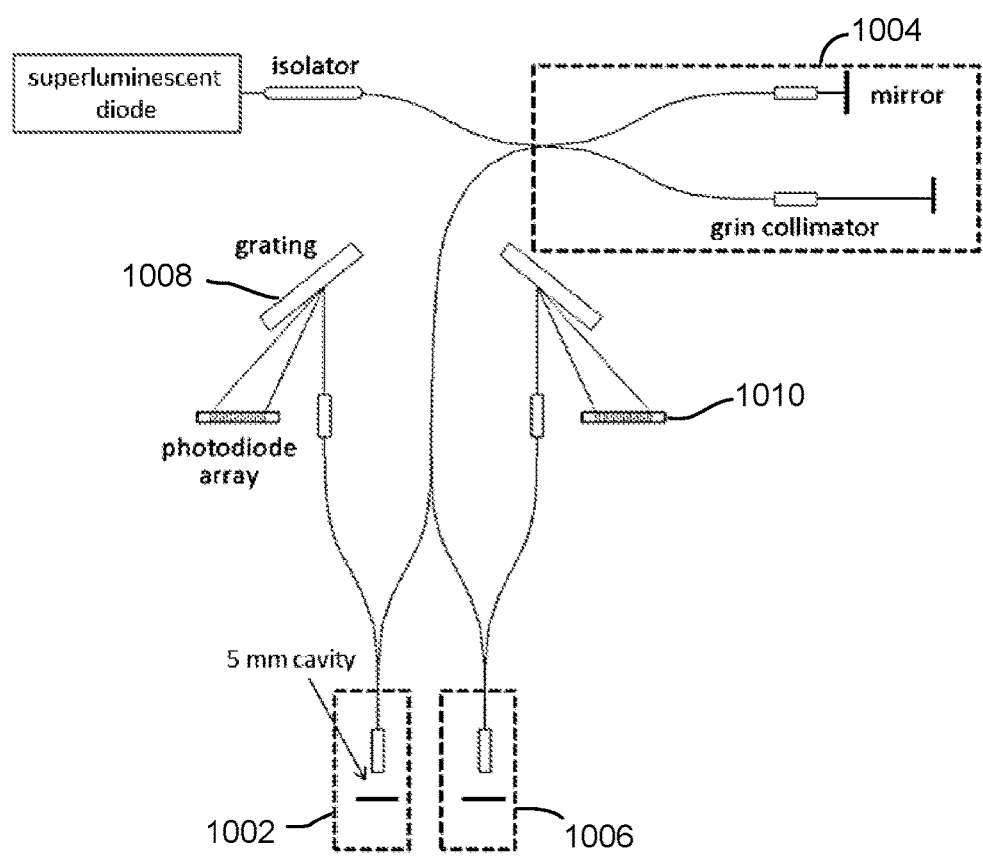
FIG. 10 illustrates a schematic of the PMDI used in our prototype including (A) the sample sensing Fabry-Perot interferometer, (B) the read-out Michelson interferometer, (C) the reference sensing Fabry-Perot interferometer, (D) and the sensing spectrometer, and (E) the reference spectrometer.

One embodiment of the system, shown in FIG. 10, employs a fiber optic path matching differential interferometer (PMDI). This type of low coherence interferometer was selected due to several advantages it has over other types of interferometers for an in situ instrument; it has the capability of performing absolute refractive index measurements; it has no moving parts; and it enables implementation a long sample path length, which contributes the sensor's excellent refractive index resolution.

A PMDI is implemented by placing two interferometers in series, one of which serves as the sensing interferometer 1002, while the other is called the read-out interferometer 1004. This embodiment has two identical sensing interferometers, 1002, 1006, both of which are in series with the same read-out Michelson interferometer (FIG. 10). One sensing interferometer 1002 monitors the fluid sample, and the other 1006 is sealed within the probe head adjacent to the sample to provide a reference signal for thermal, vibrational, and optical common mode rejection. Interference occurs in a PMDI when the read-out interferometer is adjusted such that the optical path difference between the read-out and sensing interferometers are matched such that the resolution of the detection spectrometer is capable of resolving the interference fringes. This required that the optical paths of the sensing and read-out interferometers be matched to within 150 µm.

In related embodiments, the system comprises a pressure housing, and generally disposed outside the pressure housing is a platform (e.g., block, metal block, stainless steel block) which incorporates the sample path comprising the sample sensing space (exposed or exposable to the sample) and the reference space comprising the reference path (identical to the sample path but without exposure to the sample). The fibers connecting the sample/reference paths to the internal electronic components within the pressure housing may be routed in a slot in the platform. The diffraction grating and optical detection arrays are contained with the controlling microprocessor and ADC electronics in the pressure housing as well. By keeping both sample and reference sensing spaces in close proximity, it assures that both spaces experience the same vibrational, thermal and pressure environments and thus can achieve a very high degree of "common mode rejection".

The PMDI configuration of FIG. 10 also enables the use of a fiber Fabry-Perot cavity for the sensing interferometer, which is a type of cavity specifically used in ultra-high resolution and high stability sensor applications. The inventive system's sensing cavity allows for a sample path length (L) of 5 mm or less and uses the configuration depicted in FIG. 11. Interference is produced by taking advantage of the Fresnel reflection, $I_R$, which occurs when light exits the fiber into a medium of different refractive index. In this case the reflection occurs at the glass/air boundary between the fiber and the collimator, and it serves as one arm of the interferometer. The sensing arm of the interferometer is produced when the remaining light, $I_S$, exits the fiber, travels through the sample, reflects off the mirror, and re-enters the collimator and the fiber. If $I_S$ and $I_R$ are both low intensity reflections, this cavity behaves the same as a typical two-beam interferometer, and it owes its stability to the fact that beam splitting occurs very close to the sample. Thus, path length changes occur only due to variation in the sample and small thermal changes in the collimator, which can be removed via the reference interferometer signal and calibration. Eliminating the need for the collimators and this calibration is described subsequently.

In some embodiments, the system employs another configuration where the beam width through the sample is 5 mm or less, and the sample volume is located 3 mm or less from the leading edge of the probe head in a channel which has been geometrically optimized to minimize sample disturbance. The light source suitable for use in this system is a superluminescent diode centered at 1060 nm with a bandwidth of 30 nm. In this embodiment, the detection spectrometer was built "in house" and is based on a grin (gradient index) collimator, a diffraction grating, and a 16-channel photodiode array. Data acquisition is achieved using a 20-bit current input A/D Converter (ADC) that acquires a 16-channel signal from the spectrometer at a measurement rate of 1 kHz. Various data offloading options can be implemented. The power required for the system is 4 W.

Figure 12:
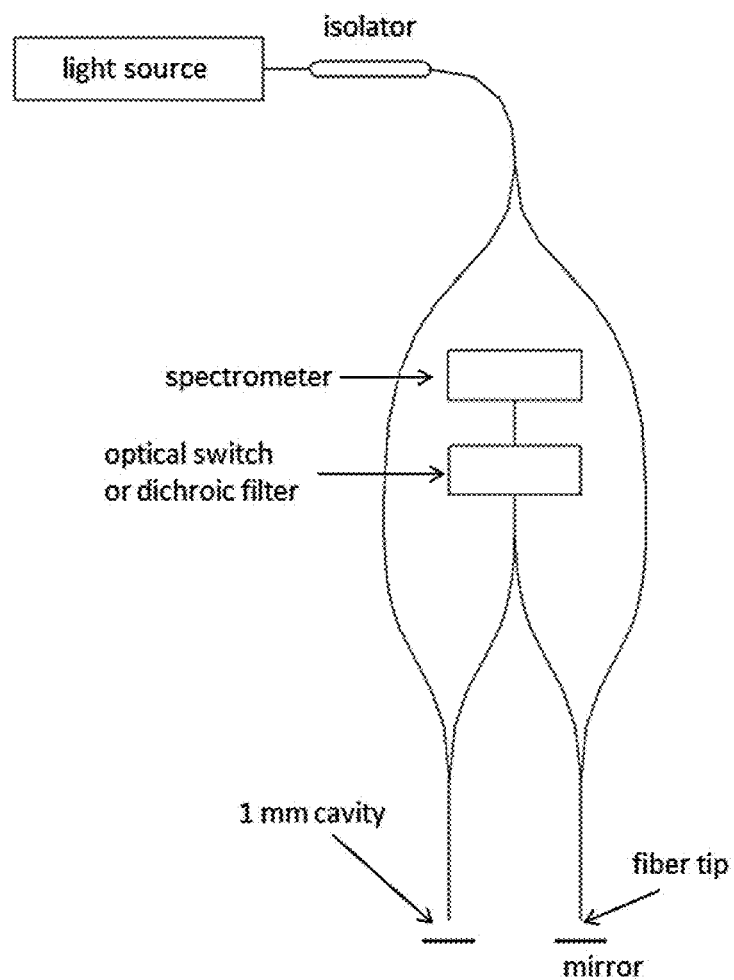
FIG. 12 depicts a schematic of the system, according to one embodiment.

In some preferred embodiments, the system is reconfigured to reduce the optical complexity of FIG. 10 by replacing the PMDI with a low coherence interferometer as shown in FIG. 12. While this configuration reduces cost, complexity, and size, it maintains the desired level of sensitivity and performance and provides a device robust enough for routine field use. The system employs a small spectrometer (e.g., detector) such as the spectrometer available from BaySpec Inc. which is approximately 2.7"×3.7" in dimensions. The configuration in FIG. 12 removes the need for an additional detector to acquire a reference measurement by incorporating an optical switch or dichroic filter. However, other embodiments may still use a second detector in communication with the reference space.

The spectral resolution of this system achieves a 1 mm sample path length without using a PMDI. While this is smaller than a 5 mm path length, the BaySpec spectrometer has 512 channels as opposed to 16 previously, which allows for averaging to overcome the loss in resolution due to the shorter path length. Also, the majority of ocean sensing applications do not require a 1 kHz sampling rate, and slower measurement rates on the order of 1-20 Hz would allow averaging across measurements to also increase resolution. In addition, the path length and greater number of channels allows imaging of more interference fringes which significantly improves absolute measurement accuracy.

The system employs the interferometric processing scheme described above to provide unprecedented range and resolution when used in conjunction with any interferometer (e.g., low coherence interferometer). Existing processing algorithms for low coherence interferometers focus on performing either low resolution absolute measurements or high resolution relative change measurements. This method is the first to combine both types of analyses in a single algorithm that achieves high resolution absolute measurements. The multiple wavelengths sampled permit unambiguous determination of the passage of fringes, eliminating the directional uncertainty at peaks and troughs with only one wavelength.

Specific simplifications resulting from the low coherence system include elimination of the read-out interferometer. In addition, the shorter path length in water and the new spectrometer make it possible to operate in the 1310 nm wavelength region rather than the 1060 nm region. This shift gives access to the arsenal of telecommunications components available in the 1310 nm spectral range. Of particular value are optical switches and dichroic filters (e.g., optical filters, thin-film filters, interference filters) that will allow use of multiplex multiple signals into one spectrometer and thus eliminate the need for two separate detection spectrometers. In another embodiment, the optical filter is replaced with a second detector.

Figure 11:
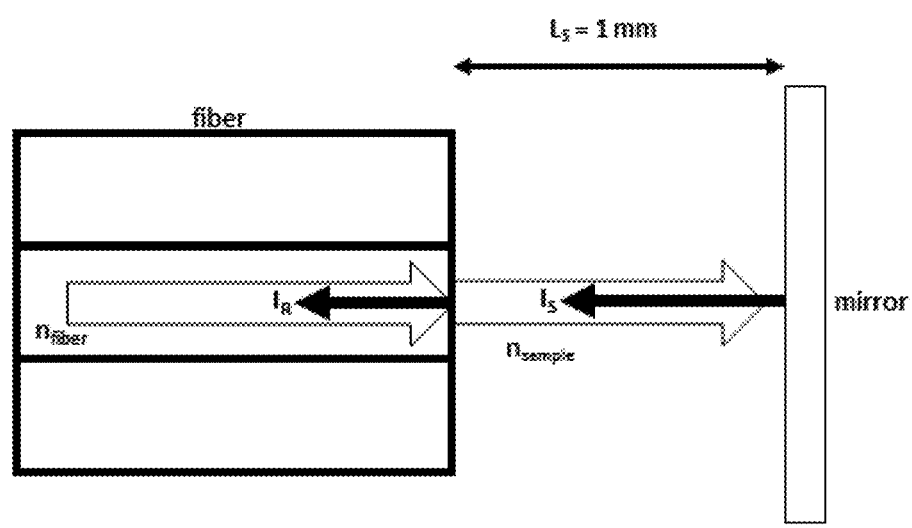
FIG. 11 depicts a Fiber Fabry-Perot interferometer. $I_R$ represents one arm of the interferometer. $I_s$ represents the second the sensing arm of the interferometer, and $n_s$ is the refractive index of the sample.
Figure 13:
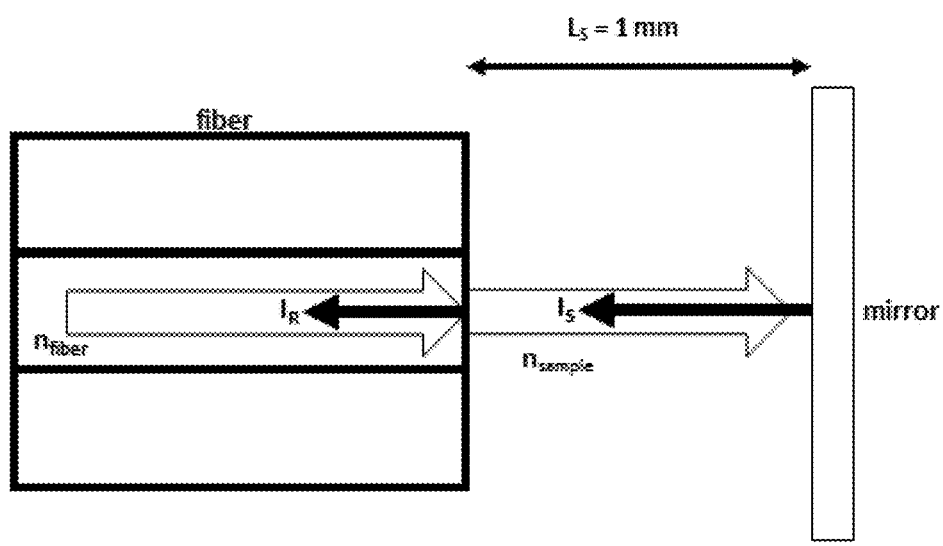
FIG. 13 depict the sample cavity and probe head including the optical concept of the sensing cavity.

The shorter 1 mm sample path length has the additional advantage of eliminating the need for the grin collimator in the sensing interferometer depicted in FIG. 11. With a short 1 mm path length, the collimator is not needed to collect a sufficient amount of the light returned from the mirror, so the mirror (or other reflective surface) can be placed directly opposite the fiber as illustrated in FIG. 13. With this setup, the split between the two arms of the interferometer occurs precisely at the fiber/sample interface, so only changes in the sample volume can affect the signal.

Figure 14:
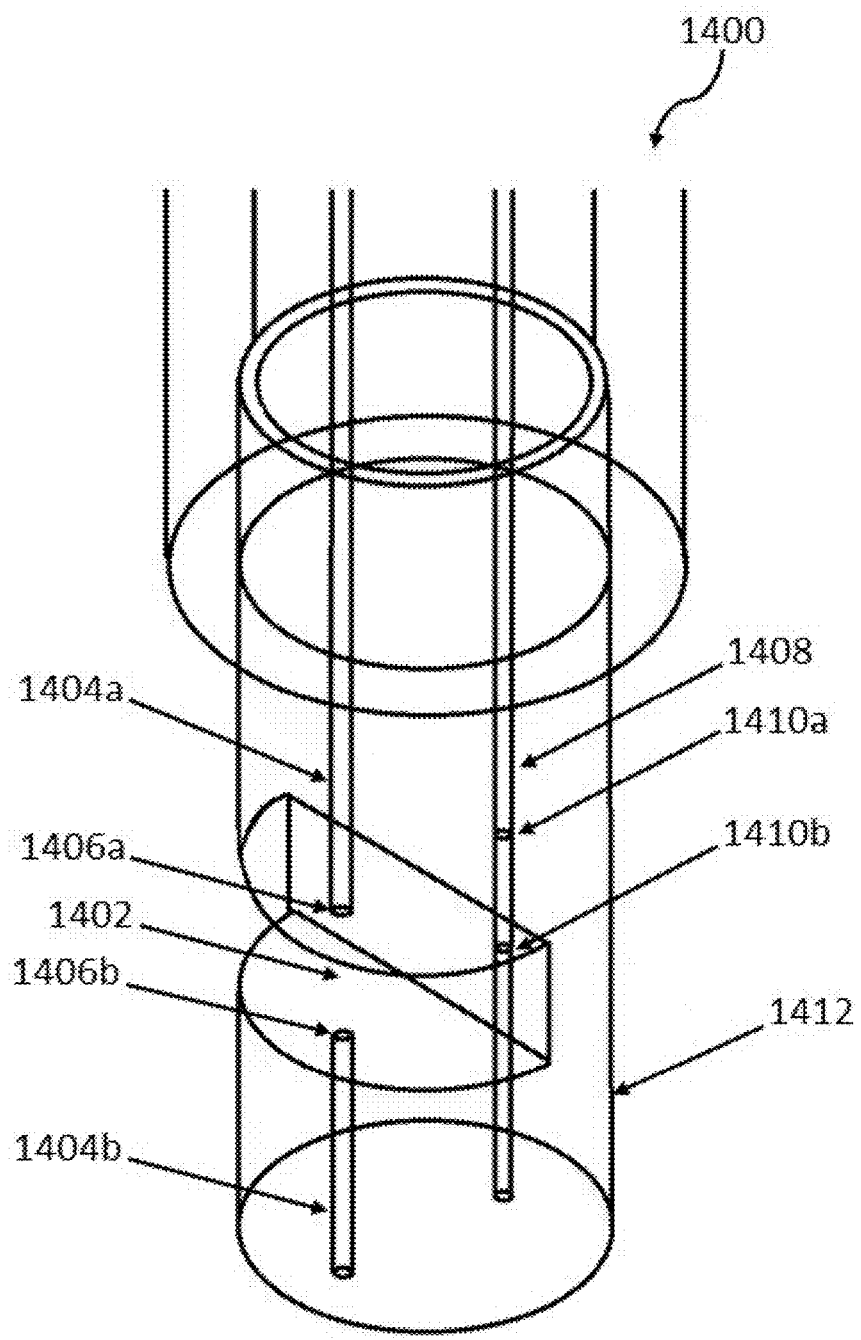
FIG. 14 illustrates the mechanical implementation of the new probe head, according to one embodiment.

As shown in the embodiment of FIG. 14, there are several mechanical developments implemented that improve the stability and robustness of the system 1400. While the sampling space 1402 can be built into a metal probe head which contains the sensing fibers 1404a and 1404b and reflective surfaces 1406a and 1406b, the metal probe head block is large due to the limited bend radius of the fibers, and the large thermal expansion of the metal affects the measurements. Although this thermal effect can be corrected using the signal from the reference fiber 1408 (e.g., reference space) and reflective surfaces 1410a and 1410b via calibration, small errors still remain. To eliminate the thermal effects and to improve the form factor of the probe head, a monolithic glass probe head may be employed using a customized fiber optic fused silica ferrule 1412. Fused silica has one of the lowest thermal coefficients of any known material and would virtually eliminate thermal expansion effects in the probe head. Also, fused silica's extremely high bulk modulus and the probe head configuration are extremely robust to high pressure. However, other materials may be used with similar strength and thermal properties as known in the art. The sensing portion of the probe head should be fully hydrostatic except for the exposed Ø125 μm face of the sensing fiber which is so small it will experience insignificant force.

In many embodiments, system 1400 operates at depths of at least 1 m, 50 m, 100 m, 500 m, 1,000 m, 2,000 m, 4,000 m, 6,000 m, 10,000 m, and full ocean depth. The simplified optics and smaller electronics of the system (detailed below) also allow for the main pressure case of the system to become significantly smaller.

For this new field-able system, an optimized electronics package is designed to be capable of real-time data collection, processing, and storage. This is particularly advantageous over systems with data acquisition and storage electronics which are produced from COTS development boards that are largely sub-optimal in terms of size and functionality. In such systems, only ADC data acquisition and storage occurs onboard the instrument, while conversion of the acquired spectrometer data to refractive index occurs in post-processing on a computer. Using a FPGA-based processor, the system acquires the interference signal, applies the inventive signal processing scheme, and stores and/or sends out refractive index values at rates up to 1 kHz.

In many embodiments, the system uses a wavelength in the range of 700 nm to 1600 nm, particularly between 1000 nm and 1500 nm, more particularly between 1100 nm and 1400 nm, and in specific embodiments, approximately 1310 nm. The 1310 nm wavelength is outside the calibration range (500-700 nm) of the Millard and Seaver (1990) formula. Although the wavelength dependence is known to be well-characterized by even powers of the wavelength, we will need to check the dependence against salinity, temperature and density requires investigation. This may be accomplished at atmospheric pressure using an available Anton-Paar DMA-5000 densitometer, accurate to 0.000005 g/cm$^3$, along with precision temperature standards and salinometers. With the 1 mm path length, it is possible to use distilled water as a calibration check point, yet still measure salinities that are well above the oceanic range.

Although the methods and systems have been described relative to specific embodiments thereof, they are not so limited. As such, many modifications and variations may become apparent in light of the above teachings. Many additional changes in the details, materials, and arrangement of parts, herein described and illustrated, can be made by those skilled in the art. Accordingly, it will be understood that the methods, devices, and systems provided herein are not to be limited to the embodiments disclosed herein, can include practices otherwise than specifically described, and are to be interpreted as broadly as allowed under the law.

We claim:

1. A system for measuring a parameter of interest in situ using a measurement of absolute optical path length difference, the system comprising:
   a radiation source adapted to emit electromagnetic radiation;
   a sample space exposed to an environmental condition and adapted to produce a fringe spectrum from the electromagnetic radiation;
   a detector capable of detecting the fringe spectrum; and
   an analysis system comprising a receiver for receiving the fringe spectrum from the detector and a sampler in communication with the receiver for selecting a first set of non-quadrature-spaced samples of the fringe spectrum, each sample corresponding to a different wavelength of light from a plurality of wavelengths;
      wherein the analysis system selects from the first set a first subset of at least three non-quadrature-spaced samples from a first fringe cycle, and a second, different subset of at least three non-quadrature-spaced samples from a second, different fringe cycle, derives a measurement of the absolute path length difference using the first and second subsets, and uses the measurement to calculate a parameter of interest.

2. The system of claim 1, wherein the analysis system derives the measurement of the absolute path length difference based on:
   (i) a base estimate of the absolute optical path length difference, based on, at least in part, the fringe spectrum, (ii) a fringe number, and (iii) a quadrant based on, at least in part, the base estimate and a reference wavelength; and
   a relative phase measurement of the absolute optical path length difference using the selected non-quadrature-spaced samples by expressing each light intensity sample as a combination comprising: (i) a term based on a relative phase φ this is based on the reference wavelength and is independent of the monitored wavelengths, and (ii) a term based on a phase shift estimate $\delta_i(L)$ relating to both the monitored wavelength corresponding to the light intensity sample and the base estimate of the absolute optical path length difference.

3. The system of claim 2, wherein the analysis system further comprises:
   a coarse estimator configured for: (a) selecting the reference wavelength in the plurality of wavelengths: and (b) determining: (i) the base estimate of the absolute optical path length difference, based on, at least in part, the fringe spectrum, (ii) the fringe number, and (iii) the quadrant based on, at least in part, the base estimate and the selected reference wavelength;
   a relative phase estimator for determining the relative phase measurement of the absolute optical path length difference using the selected non-quadrature- spaced samples; and
   an aggregator for deriving the measurement of the absolute optical path length difference by aggregating the relative phase measurement, the fringe number, and the quadrant.

4. The system of claim 1 wherein the sample space comprises an external fluid environment.

5. The system of claim 1, wherein a number of wavelengths in the plurality of wavelengths ranges from 3 up to 4096, and the fringe spectrum comprises a plurality of fringe cycles, and a number of fringe cycles is up to 2048.

6. The system of claim 1, wherein the parameter of interest is selected from the group comprising of salinity, pressure, density, temperature, strain, vibration, distance, refractive index of a medium, and changes thereof.

7. The system of claim 1, wherein the plurality of wavelengths range from a low wavelength up to a high wavelength that is greater than the low wavelength by a bandwidth, the low wavelength ranges from 600 nm up to 1590 nm, and the high wavelength ranges from 610 nm up to 1600 nm; and the bandwidth ranges from 10 nm up to 200 nm.

8. The system of claim 1, wherein the radiation source adapted to emit at least N wavelengths of electromagnetic radiation, wherein N is greater than two.

9. The system of claim 1, wherein system is capable of measuring the parameter of interest of a body of water.

10. The system of claim 1, wherein the system is capable of operating at a depth of at least 1 m, 50 m, 100 m, 500 m, 1,000 m, 6,000 m, and full ocean depth.

11. The system of claim 1, wherein the system is adapted for use on a vehicle, a water sampler, a profiler, an underwater observatory, and in a sensor array.

12. The system of claim 1, wherein the sample space comprises a sample path length between 5 mm and 200 µm.

13. The system of claim 1 further comprising one of an optical switch, an optical filter, a dichroic filter, and a second detector.

14. The system of claim 1, wherein the system produces a high resolution absolute optical path length difference measurement of $1/1,000$-th up to $1/100,000$-th of a wavelength.

15. The system of claim 1 further comprising a pressure housing.

16. The system of claim 1, further comprising:
   a second sample space exposed to a second environmental condition and adapted to produce a second fringe spectrum using the electromagnetic radiation,
   wherein:
      the detector is adapted for detecting the second fringe spectrum;
      the a receiver is adapted for receiving the second fringe spectrum from the detector;
      the sampler is adapted for selecting a second set of non-quadrature-spaced samples of the second fringe spectrum; and
      the analysis system derives a measurement of a second absolute path length difference and uses the measurement of the second absolute path length difference to calculate a second parameter of interest corresponding to the second environmental condition.

* * * * *